United States Patent
Subhash et al.

(10) Patent No.: US 11,660,465 B2
(45) Date of Patent: May 30, 2023

(54) SKIN CARE IMPLEMENT AND SYSTEM

(71) Applicant: Colgate-Palmolive Company, New York, NY (US)

(72) Inventors: Hrebesh Molly Subhash, Somerset, NJ (US); Deborah Ann Peru, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 656 days.

(21) Appl. No.: 16/619,658

(22) PCT Filed: Jun. 13, 2018

(86) PCT No.: PCT/US2018/037186
§ 371 (c)(1),
(2) Date: Dec. 5, 2019

(87) PCT Pub. No.: WO2018/236629
PCT Pub. Date: Dec. 27, 2018

(65) Prior Publication Data
US 2020/0179713 A1     Jun. 11, 2020

Related U.S. Application Data

(60) Provisional application No. 62/522,545, filed on Jun. 20, 2017, provisional application No. 62/522,535, (Continued)

(51) Int. Cl.
*A61N 5/06* (2006.01)
*A61B 5/00* (2006.01)
*A61N 5/067* (2006.01)

(52) U.S. Cl.
CPC .......... *A61N 5/0616* (2013.01); *A61B 5/0077* (2013.01); *A61B 5/445* (2013.01);
(Continued)

(58) Field of Classification Search
CPC ... A61N 5/06–2005/073; A61B 5/0077; A61B 5/445; A61B 5/4836;
(Continued)

(56) References Cited

U.S. PATENT DOCUMENTS 8,702,772 B2 * 4/2014 Luzon ..................... A61B 5/44
                                                      607/89
8,709,003 B2   4/2014 Island et al.
(Continued)

FOREIGN PATENT DOCUMENTS

CN     101181114     5/2008
CN     104587610     5/2015
(Continued)

OTHER PUBLICATIONS

International Search Report and Written Opinion of the International Searching Authority in International Application No. PCT/US2018/037186, dated Nov. 16, 2018.
(Continued)

*Primary Examiner* — Jonathan T Kuo

(57) ABSTRACT

In one embodiment, a personal care implement is disclosed. The personal care implement has an emitting end and an electromagnetic source for projecting electromagnetic radiation onto an area of skin to treat a skin condition. A light sensor is configured to sense an amount of ambient light present at the emitting end. A controller instructs the electromagnetic source to begin projecting only when the light sensor senses that the amount of ambient light at the emitting end is below a predefined threshold.

10 Claims, 24 Drawing Sheets

Related U.S. Application Data filed on Jun. 20, 2017, provisional application No. 62/522,526, filed on Jun. 20, 2017.

(52) U.S. Cl.
CPC .... *A61B 5/4836* (2013.01); *A61B 2560/0431* (2013.01); *A61B 2576/02* (2013.01); *A61N 5/067* (2021.08); *A61N 2005/0628* (2013.01); *A61N 2005/0652* (2013.01)

(58) Field of Classification Search
CPC ........ A61B 2560/0431; A61B 2576/02; A61B 2018/00452; A61B 2018/00904
See application file for complete search history.

(56) References Cited

U.S. PATENT DOCUMENTS

| | | | |
|---|---|---|---|
| 10,092,449 B2 * | 10/2018 | Kelleher | A61F 9/009 |
| 2007/0049910 A1 | 3/2007 | Altshuler et al. | |
| 2008/0319430 A1 | 12/2008 | Zenzie et al. | |
| 2009/0143842 A1 | 6/2009 | Cumbie et al. | |
| 2013/0344454 A1 | 12/2013 | Nath | |
| 2014/0074193 A1 * | 3/2014 | Luzon | A61B 18/203 607/88 |
| 2015/0005750 A1 * | 1/2015 | Kelleher | A61F 9/0079 606/27 |
| 2015/0182757 A1 | 7/2015 | Levine et al. | |
| 2015/0230863 A1 * | 8/2015 | Youngquist | A61B 18/203 606/9 |
| 2016/0184566 A1 | 6/2016 | Ibrahim et al. | |

FOREIGN PATENT DOCUMENTS

| | | |
|---|---|---|
| WO | 2005/065777 | 7/2005 |
| WO | 2007/016634 | 2/2007 |
| WO | 2009/016963 | 2/2009 |
| WO | 2012/146256 | 11/2012 |
| WO | 2017/019839 | 2/2017 |
| WO | 2017/030768 | 2/2017 |

OTHER PUBLICATIONS

Kangwei et al., "Cosmetics and Skin Care," Fujian Science & Technology Publishing House, Jun. 1988, p. 84, including English machine translation, pp. 1-9.

* cited by examiner

SKIN CARE IMPLEMENT AND SYSTEM

CROSS REFERENCE TO RELATED APPLICATIONS

The present application is filed under 35 U.S.C. 371 claiming benefit of PCT Application No. PCT/US2018/ 037186, filed Jun. 13, 2018, which claims the benefit of U.S. Provisional Application No. 62/522,526, filed Jun. 20, 2017, U.S. Provisional Application No. 62/522,535, filed Jun. 20, 2017, and U.S. Provisional Application No. 62/522,545, filed Jun. 20, 2017, the disclosures of which are incorporated herein by reference in their entireties.

BACKGROUND

Acne is a complex skin health condition which affects a broad population of teens and young adults. Clinically, acne is described as a disease of features known as pilosebaceous units (PSUs), which are located under the superficial skin surface, especially on the face, upper back, and chest, and contain sebaceous glands that are connected to hair follicles. Acne can cause persistent hyperpigmentation and psychological sequelae, and require an individualized and customized treatment regime. Untreated, acne can lead to significant physical, emotional, and social problems. These problems are preventable if the disease is treated early. But acne is both progressive and cumulative, becoming more complex and costly to treat over time. At worst, untreated acne may lead to irreversible damage over the lifespan. Prevention, early intervention, and management are critical to avoid the long-term negative effects of acne. But there is currently no low-cost, at-home imaging device or method available for the early detection, monitoring, and/or treatment of acne for personal and point-of-care applications outside of the professional dermatology office setting.

Further, various methods can be used to monitor skin health. Existing methods, however, do not track changes to skin health over time. For example, such methods cannot determine whether a skin treatment routine is being effective over a period of time. Thus, there is need for a system and method for monitoring changes in skin health, and for basing a skin treatment routine or evaluation on such changes.

BRIEF SUMMARY

The present disclosure provides solutions to the above described problems. The disclosure is divided into three sections. Section I discusses a hand-held personal care implement using light treatment, which can include a safety mechanism for controlling when light is emitted. Section II discusses a system and method for stitching images together to create a composite image, such as images of the skin taken by a hand-held personal care implement. Section III discusses monitoring changes to the skin and, based on the changes, determining a skin evaluation or a suggested treatment routine, and/or providing feedback on how well a routine is being followed. Different embodiments disclosed in the respective sections can be used together as part of a personal care apparatus, method, or system. To the extent a term, reference number, or symbol is used differently in different sections, context should be taken from the relevant section and not the other sections.

BRIEF DESCRIPTION OF THE DRAWINGS

The present disclosure will become more fully understood from the detailed description and the accompanying drawings, wherein.

DETAILED DESCRIPTION

Figure 1:
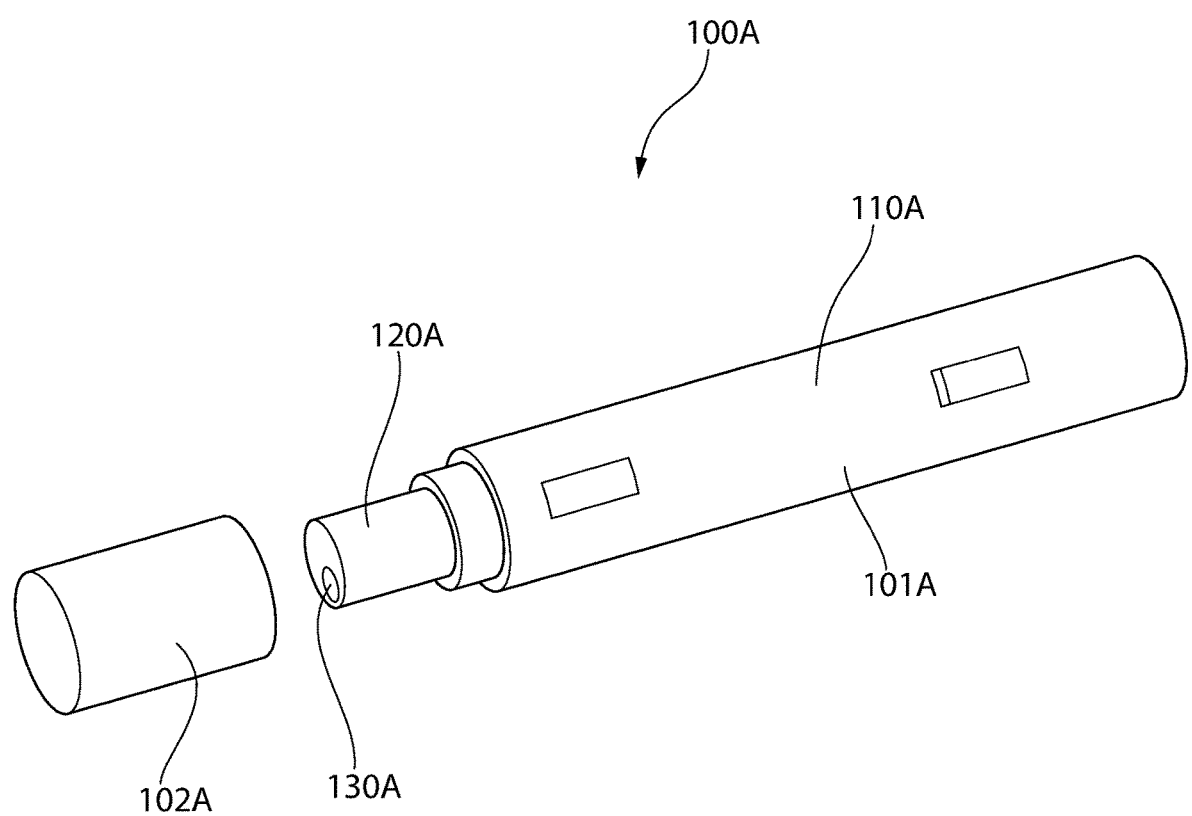
FIG. 1 is a front perspective view of a personal care implement according to exemplary embodiments of the invention.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and other similar terms refer to a relationship wherein structures are secured or attached to one another either directly or indirectly through intervening structures, as well as both movable or rigid attachments or relationships, unless expressly described otherwise. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

Features of the present invention may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Section I

To address the need discussed above, the claimed invention is directed to the development of a miniature, cost effective and safe optical imaging device and treatment method for consumer level applications, for example. While the invention is described with regard to a personal care implement that uses light to treat skin conditions, it is noted that other non-limiting examples of personal care implements include other personal care or personal therapeutic products.

Exemplary embodiments of the invention relate to a consumer-level device that can be used as a stand-alone device for monitoring acne distribution for at-home diagnostics for use in the application of acne specific facial cleansers. Other embodiments of the device combine a special active ingredient to treat acne using light activated photodynamic therapy (PDT). The device can image the potential acne-prone sites on the face (and other areas) by targeting fluorescence emission of the metabolic byproduct of pAcnes (*Propionibasterium acnes*) and transmits the information to a smart phone or other portable electronic device to analyze and interpret the image and, consequently, acts as an early detection system for the consumer to prevent the proliferation in advance by the topical administration of anti-acne cleansers.

Some embodiments work in combination with skin care products specifically formulated with a photosensitizer composition that works to eradicate pAcnes bacteria in conjunction with an electromagnetic radiating source, for example a laser (light amplification by stimulated emission of radiation) light source of specific wavelength.

In one aspect, the invention is directed to a personal care implement. The personal care implement includes an emitting end; an electromagnetic source for projecting electromagnetic radiation onto an area of skin, the electromagnetic source having emission characteristics to treat a skin condition; a light sensor configured to sense an amount of ambient light present at the emitting end; and a controller that instructs the electromagnetic source to begin projecting only when the light sensor senses that the amount of ambient light at the emitting end is below a predefined threshold.

In another aspect, the invention may be a method of preventing an electromagnetic source from projecting from a hand-held personal care implement. The method includes providing the hand-held personal care implement with an emitting end, an electromagnetic source for projecting electromagnetic radiation onto an area of skin, a light sensor configured to sense an amount of ambient light present at the emitting end, and a controller; and beginning to project the electromagnetic radiation onto the area of skin only when the light sensor of the personal care implement senses the amount of ambient light at the emitting end of the personal care implement is below a predefined threshold.

In another aspect, the invention may be a method of treating a skin condition at a treatment area on skin of a user using a hand-held personal care implement. The method includes holding the hand-held personal care implement in the hand of the user; moving the personal care implement into contact with the skin of the user; beginning to project a treatment light source of the personal care implement onto the treatment area of the skin only when a light sensor of the personal care implement senses an amount of ambient light at a treatment end of the personal care implement is below a predefined threshold.

In another aspect, the invention may be a personal care implement including an emitting end; an electromagnetic source; a light sensor configured to sense an amount of ambient light present at the emitting end; and a controller that instructs the electromagnetic source to begin projecting only when the light sensor senses the amount of ambient light at the emitting end is below a predefined threshold.

In another aspect, the invention may be a personal care implement including a body section; a treatment section having a treatment end and a body end, the treatment end being located at a distal end of the treatment section and opposite the body end, the body end being attached to the body, the treatment end being formed as a seal; a treatment light source for projecting treatment light onto a treatment area, the treatment light source having emission characteristics to treat a skin condition; a light sensor configured to sense an amount of ambient light present at the treatment end of the treatment section; and a controller that instructs the treatment light source to be in an off position when the light sensor senses the amount of ambient light at the treatment end of the treatment section is above a predefined threshold.

In another aspect, the invention may be a personal care implement including a body section; a treatment section having a treatment end and a body end, the treatment end being located at a distal end of the treatment section and opposite the body end, the body end being attached to the body, the treatment end being formed as a seal; a treatment light source for projecting treatment light onto a treatment area, the treatment light source having emission characteristics to treat a skin condition; a light sensor configured to sense an amount of electromagnetic radiation at the treatment end of the treatment section; and a controller that instructs the treatment light source to begin projecting the treatment light only when the light sensor senses the amount of electromagnetic radiation at the treatment end of the treatment section is below a predefined threshold.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

FIG. 1 is a schematic example of a personal care implement in the form of an acne analysis and treatment device. Device 100A includes, in this example, a main portion 101A and a cap 102A that is provided to protect certain elements of device 100A when not in use. Main portion 101A includes a body 110A that can be configured to be comfortably held by the hand of a user. Body 110A is, in this example, pen-like and is compact for ease of handling and storage. Body 110A includes various switches including, for example, an on-off switch, an operating mode switch, and a light intensity switch. Body 110A can house a battery (not shown), either single use or rechargeable, for powering the various functional elements of device 100A. Device 100A also includes a treatment section 120A that is attached to one end of body 110A. Treatment section 120A (and/or body 110A) contains the various functional elements for performing the treatment. Treatment section 120A, in this example, includes a transmission port 130A through which electromagnetic radiation (for example a laser beam) can pass to provide treatment to the area to be treated. Port 130A can be an opening or can be a transparent element that permits the desired electromagnetic radiation to pass through port 130A.

Figure 2:
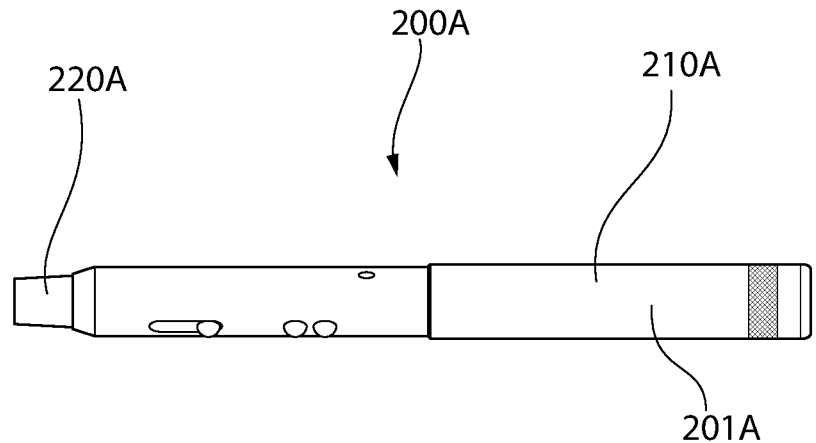
FIG. 2 is a side view of a personal care implement according to exemplary embodiments of the invention.
Figure 3:
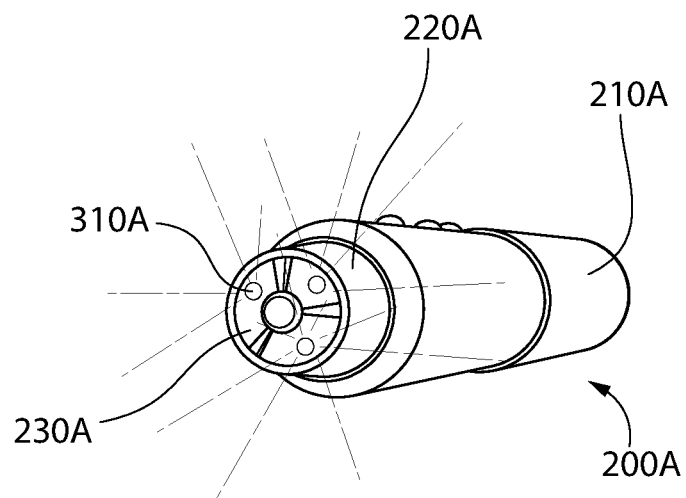
FIG. 3 is a front perspective view of the personal care implement shown in FIG. 2.

FIGS. 2 and 3 show another example of a personal care implement in accordance with embodiments of the invention. In this example, personal care implement 200A has a main portion 201A that includes a body 210A that is cylindrical and pen-like. It is noted that other configurations of personal care implement 200A and body 210A can also be provided. For example, body 210A can be triangular or square (or another polygon) in cross-section or contain a flat region to help prevent implement 200A from rolling on a flat surface. Body 210A includes various switches including, for example, an on-off switch, an operating mode switch, and a light intensity switch. Body 210A can also have a clip or other feature for clipping implement 200A on a pocket, folder, or other item. Attached to one end of body 210A is a treatment section 220A. Treatment section 220A has an emitting end (hereinafter referred to as a treatment end) that is configured to come in contact with the treatment area of the skin that is to be treated. In this example, treatment section 220A has an opening 230A that allows light from treatment light sources 310A to project out of treatment section 220A and onto the treatment area. In this example, treatment light sources 310A are laser light sources. In other examples, other forms of electromagnetic radiation are used instead of, or in conjunction with, laser light sources 310A.

As briefly described above, personal care implements in accordance with the invention can be used with a sensitizing agent to treat acne. The sensitizing agent can be, for example, either aminolevulinic acid (ALA) or methylaminolevulinate (MAL). In exemplary practices, ALA is applied to the skin for a 30-90 minute incubation time for the treatment of actinic keratosis. ALA and MAL when applied to the skin accumulate preferentially in sebaceous (oil) glands and the epidermis, as well as in pAcne bacteria, which allows the applied light to target the acne. After a short incubation period (such as the 30-90 minutes described above) the active ingredient is activated with laser light sources 310A. As an alternative to a laser light source, a blue light source can be used. The resulting decrease in sebaceous glands and pAcne bacteria can lead to significant acne improvement.

Professional skin care topicals designed for use with light emitting diode or laser light are currently available and sold for in-office treatments. The formulas containing 5-aminolevulinic acid, a photosensitizing agent or an equivalent ingredient, is an effective treatment of mild to moderate acne. In this treatment modality, when 5-aminolevulinic acid is applied to skin lesions it is absorbed and converted to protoporphyrin IX (a photosensitive compound). When light of the appropriate wavelength activates protoporphyrin IX, abnormal cells are selectively destroyed. The light used is preferably at a wavelength near the peak of porphyrin absorption in tissue. The Soret band at 405-420 nm is the peak of protoporphyrin IX absorption. However, there is also a weaker absorbance around 590-645 nm that may also be used. As a result, laser (or other) light sources having wavelengths in these ranges are preferable for achieving the desired results.

Following light activation, porphyrins are excited to a higher energy state, which can result in generation of reactive oxygen species, such as singlet oxygen or free radicals. Porphyrins from ALA are concentrated near mitochondria, leading to cell death of malignant or pre-malignant cells upon light exposure. For the treatment of acne, preferential accumulation of ALA in sebaceous glands as well as reduction in *Propionibacterium acnes*, the bacteria implicated in acne, are thought to be the responsible mechanisms. For treatment of photoaging, increased collagen synthesis following ALA photodynamic therapy may play a role.

Figure 4:
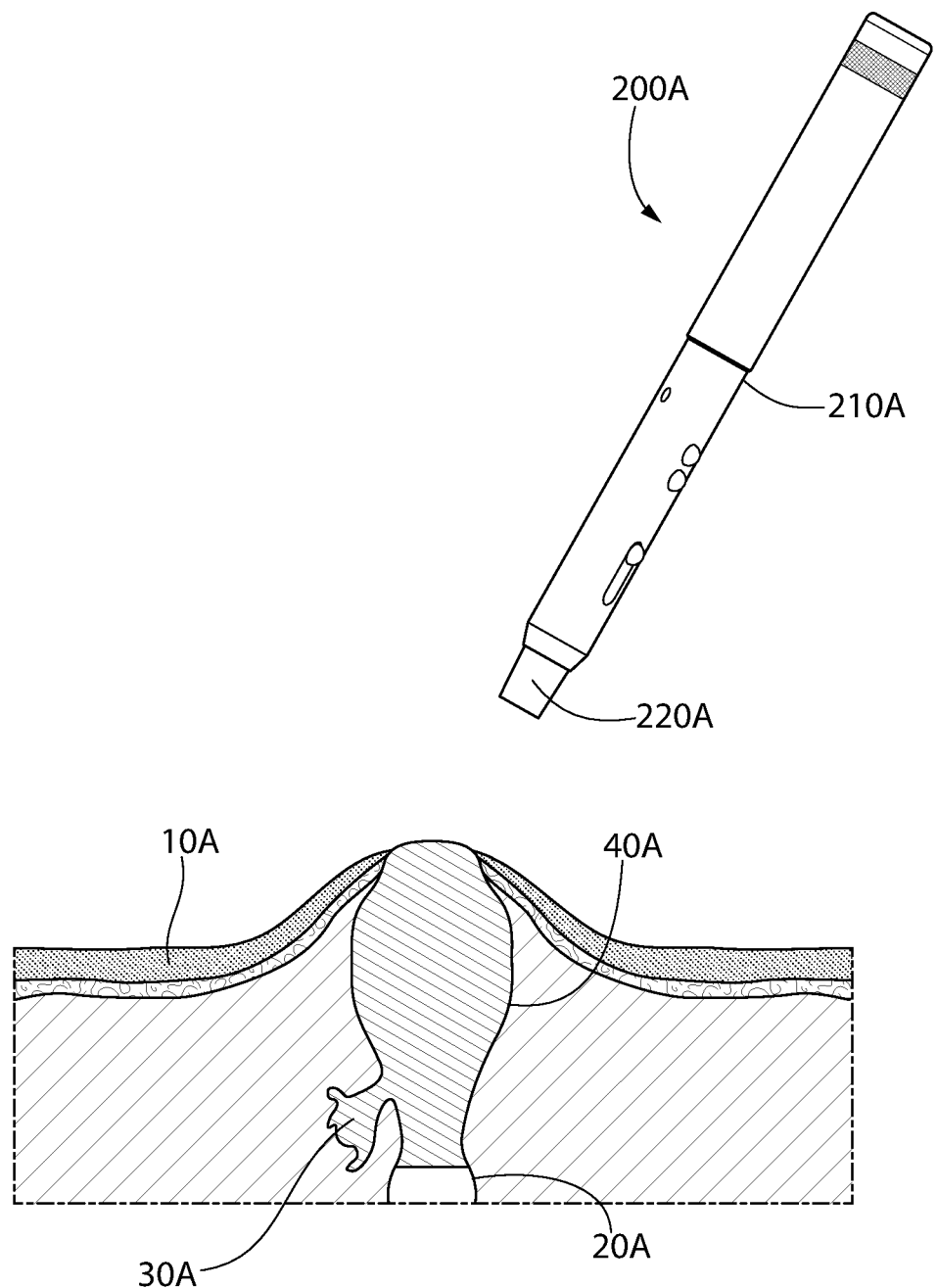
FIG. 4 is a front view of the personal care implement shown in FIG. 2 being moved toward a treatment area.
Figure 5:
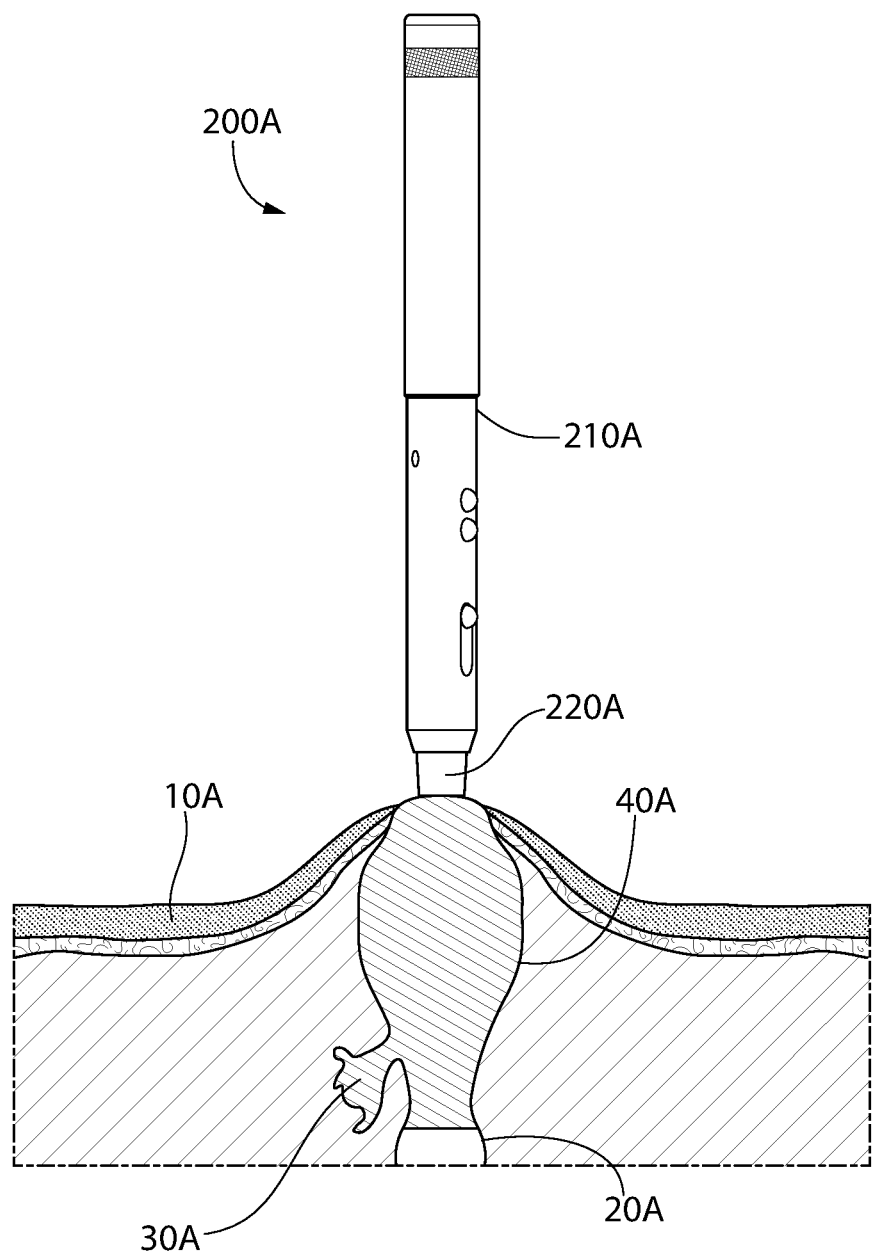
FIG. 5 is a front view of the personal care implement shown in FIG. 4 in position on a treatment area.

FIG. 4 shows personal care implement 200A being moved toward an acne lesion that has resulted from a hair follicle 20A and its associated sebaceous (oil) gland 30A being blocked with sebum and blood toxins 40A. FIG. 5 shows personal care implement 200A in place on the acne lesion in the proper position for treatment. In this embodiment, treatment section 220A is attached to body 210A in a spring-loaded telescoping manner. When implement 200A is pressed onto the skin, treatment section 220A slides against a spring force into body 210A. This is shown in FIG. 5 as the portion of treatment section 220A that extends from body 210A is shorter than that shown in FIG. 4. This produces pressure sufficient to create a seal between the end of treatment section 220A and skin 10A. This seal is preferably sufficient to prevent ambient light from entering the inside area of treatment section 220A. Some embodiments provide a rubber or other resilient seal at the edge of treatment section 220A to facilitate a light-proof seal. Other embodiments provide no specific sealing material and rely on sufficient pressure being exerted to press the edge of treatment section 220A against the skin.

Because laser light can be harmful to humans (and other animals), particularly to the eyes, it is desirable to provide safety measures to prevent laser light from escaping from implement 200A in any damaging way. If the laser light of implement 200A could be turned on simply by activating a switch, laser light could be projected into the eyes of a user or someone else nearby, potentially causing damage. To avoid this problem, the invention includes a safety mechanism that prevents activation of the laser (or other) treatment light source until implement 200A is properly positioned to treat the treatment area.

Figure 6:
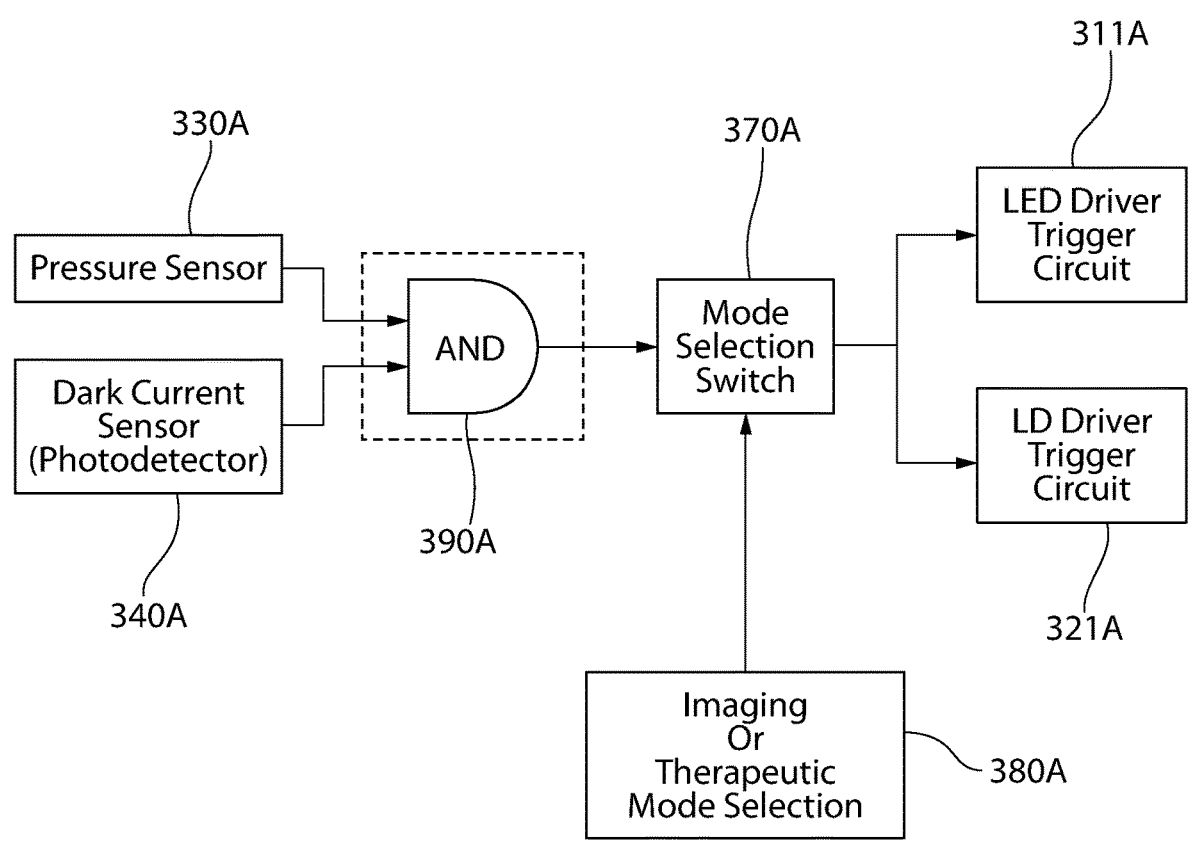
FIG. 6 is a schematic diagram of exemplary embodiments of the invention.

FIG. 6 is a schematic chart that shows an exemplary controller circuit that can be used in implement 200A. A pressure sensor 330A can be provided to determine whether treatment section 220A is being pressed against a surface such as, for example, the skin of a user. A dark current sensor (or photodetector) 340A is provided to measure the level of light at the end of treatment section 220A. Dark current sensor (or photodetector) 340A can, in some embodiments, distinguish between ambient light (or other light) and laser treatment light (or other electromagnetic radiation) in order to determine if ambient light is entering treatment section 220A regardless of whether treatment light or other electromagnetic radiation is present. If treatment section 220A has an opening (like, for example, opening 230A in FIG. 3) then dark current sensor 340A will measure the light present inside treatment section 220A. If implement 200A is pressed sufficiently against the skin, the edge of treatment section 220A will form a light-proof (or near light-proof) seal with the skin. This seal will prevent ambient light outside of treatment section 220A from entering the inner area of treatment section 220A. This absence of light will cause the dark current sensor to output a signal indicating such. Logical AND operator 390A receives signals from pressure sensor 330A and dark current sensor 340A. If pressure sensor 330A indicates pressure above the predetermined threshold and dark current sensor 340A indicates a sufficient lack of light, then logical AND operator 390A will provide a signal to a mode selection switch 370A that permits operation of mode selection switch 370A. In some embodiments, mode selector switch can be set to either an imaging mode or a therapeutic mode. The imaging mode is not the subject of this application. The therapeutic mode is the mode discussed above that projects laser light, or other electromagnetic radiation, onto a treatment area. Depending on the mode selected with mode selection switch 370A, an LED (light emitting diode) trigger circuit 311A activates one or more LEDs, and/or an LD (laser device) driver trigger circuit 321A activates one or more laser lights. The LEDs can be for imaging or for simply providing light to the treatment area so that the user can properly position implement 200A. The LDs (or other electromagnetic radiation sources) provide the light to activate the photosensitizing agent discussed above. While this example includes both pressure sensors and dark current sensor(s), it is noted that some embodiments use only pressure sensor(s) and some embodiments use only dark current (or other light) sensor(s).

In some embodiments, the treatment light is immediately shut off upon sensing of light above the acceptable threshold and/or sensing of pressure below the acceptable threshold. These embodiments shut off the treatment light regardless of whether or not treatment has been completed. Other embodiments include a timer that keeps the treatment light on (once activated) for a set period of time (for example 30 seconds) regardless of whether or not the light and/or pressure thresholds are crossed. In particular embodiments, the light and/or pressure thresholds must be satisfied to turn the treatment light on, but they do not need to be maintained once the timer starts. The advantage of these timer-controlled embodiments is that a slight lifting of the implement from the skin will allow treatment to continue once started. It is believed that the risk of accidentally exposing an eye to the treatment light once the implement has been properly located and treatment has started is very low.

Figure 8:
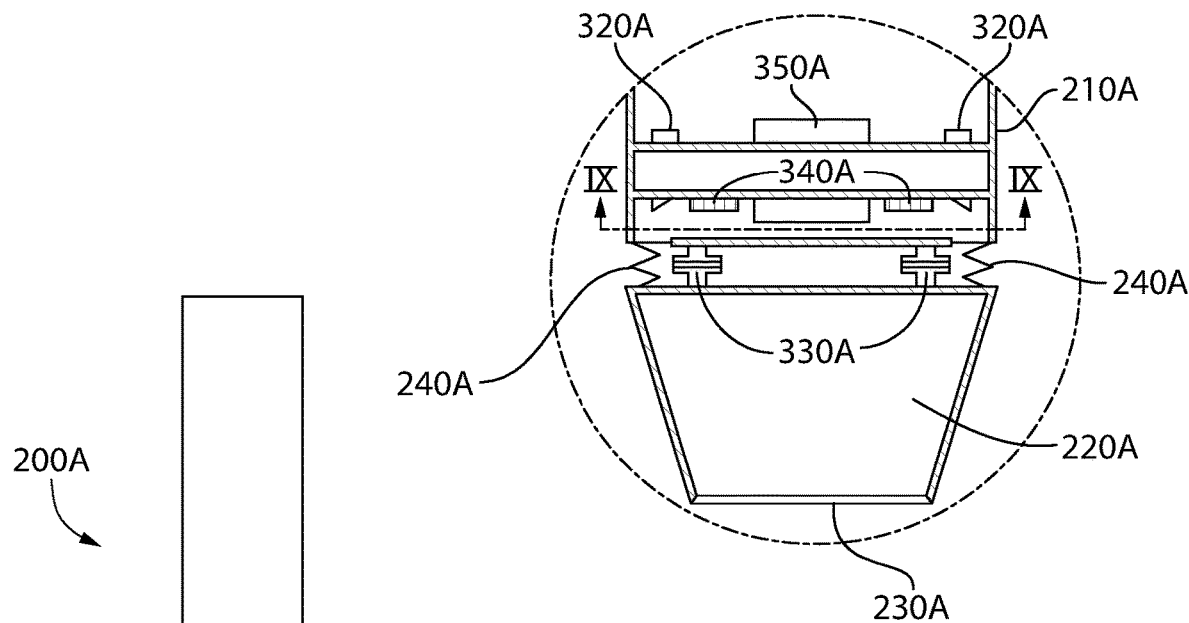
FIG. 8 is partial view of the personal care implement shown in FIG. 7.
Figure 7:
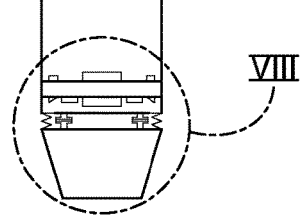
FIG. 7 is a side view of a personal care implement according to exemplary embodiments of the invention.
Figure 9:
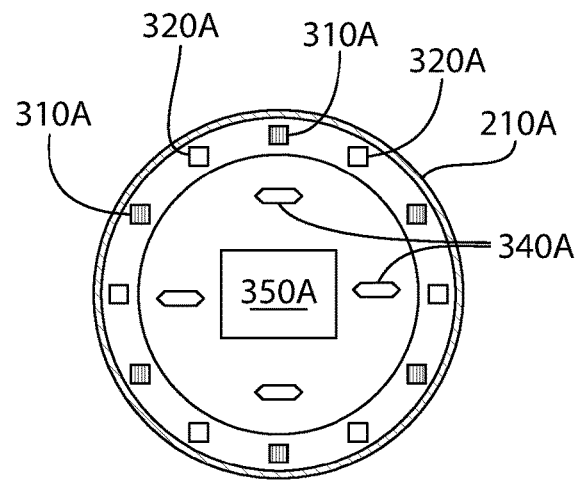
FIG. 9 is an end view of the personal care implement shown in FIG. 7.

FIGS. 7-9 show an example of personal care implement 200A for the treatment of a skin condition. In this embodiment, treatment section 220A is a frustoconical tube that includes opening 230A at its distal end. Other shape hollow structures can be used for treatment section 220A as long as light can pass through the central volume of treatment section 220A but preferably not through the sides of treatment section 220A. Treatment section 220A can also be a solid as long as light can pass through the central volume of treatment section 220A but preferably not through the sides of treatment section 220A. In the case of a sold, a translucent or transparent glass or plastic with or without a coating on its side surfaces can be used, for example.

In this example, four photodetectors 340A are provided to measure the amount of light inside treatment section 220A. As mentioned above, photodetectors 340A can be dark current sensors or some other type of light sensor. For example, a camera can measure dark current and thereby function as a photodetector for detecting ambient light. The purpose of photodetectors 340A is to determine whether implement 200A, particularly treatment section 220A, is properly sealed against the skin to prevent treatment light from exiting treatment section 220A. The logic is that if no ambient light enters treatment section 220A then it must be sufficiently sealed against the skin to prevent treatment light form exiting treatment section 220A. Although four photodetectors 340A are shown in this example, fewer or more photodetectors can be used. Also, the location and orientation of photodetectors 340A are exemplary only. Other locations and orientations can be used.

In this example, six LEDs 310A and six laser light sources 320A are provided in a ring orientation such that they project toward opening 230A of treatment section 220A. The LEDs illuminate the treatment area for one or more purposes such as, for example, to assist the user in identifying the location of the treatment area and/or to brightly illuminate the treatment area for imaging. Although LEDs are used in this example due to their small size and efficient use of electric power, other light sources can be used. Laser light sources 320A provide the treatment light discussed above that can activate the photosensitizing agent. Element 350A represents an imaging sensor that can be used for imaging of the treatment area.

FIG. 8 shows two pressure sensors 330A that are used to sense pressure exerted on treatment section 220A by its contact with the skin of the user. In this example, as treatment section 220A contacts the skin and body 210A is pressed further toward the skin, bellows 240A permit treatment section 220A to move relative to body 210A. This movement is detected by pressure sensors 330A. When pressure sensors 330A indicate a pressure at or above a predetermined threshold pressure, a light-tight seal between treatment section 220A and the skin is considered made. Although bellows are shown in this example, they are only representative of many mechanical couplings that are possible. For example, a telescoping coupling or a pivoting coupling can be used. Other embodiments use a solid connection with stress sensors used as the pressure sensors. These examples are illustrative only and are not limiting or exclusive.

Figure 10:
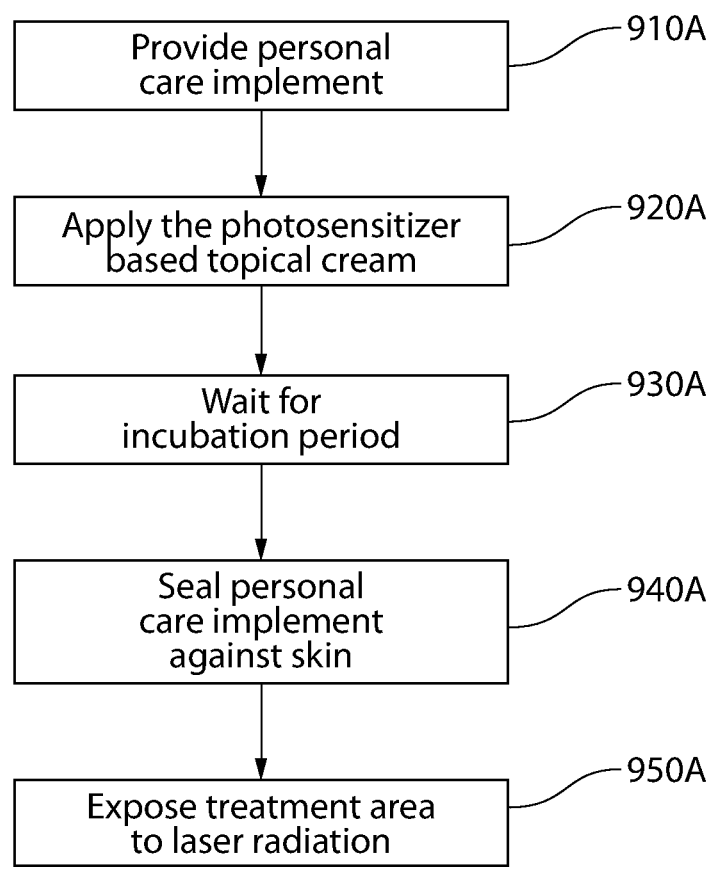
FIG. 10 is a flow chart in accordance with exemplary embodiments of the invention.

FIG. 10 shows an exemplary method of treating skin in accordance with embodiments of the invention. In step 910A a personal care implement such as the examples discussed above is provided. In step 920A a photosensitizer based topical cream is applied to the treatment area of the skin. In step 930A an incubation period is allowed to pass before proceeding. The incubation period is the period of time the photosensitizing cream requires to properly be absorbed by the tissues that are to be destroyed (discussed above). Once the incubation period has passed, the personal care implement is pressed against the skin to create a light-proof seal around the treatment area in step 940A. Once the proper seal is made, as indicated by the photodetector(s) and/or pressure sensor(s), the treatment area is exposed to the laser (or other) radiation to active the photosensitizing cream and therefore treat the skin condition.

As can be seen from this disclosure, the invention provides a solution to at least the problem of safely exposing skin to laser radiation for the treatment of a skin condition.

Example Claims

Example Claim 1: A personal care implement comprising: an emitting end; an electromagnetic source for projecting electromagnetic radiation onto an area of skin, the electromagnetic source having emission characteristics to treat a skin condition; a light sensor configured to sense an amount of ambient light present at the emitting end; and a controller that instructs the electromagnetic source to begin projecting only when the light sensor senses that the amount of ambient light at the emitting end is below a predefined threshold.

Example Claim 2: The personal care implement of claim 1, further comprising a body section; a treatment section including the emitting end and a body end, the emitting end being located at a distal end of the treatment section and opposite the body end, the body end being attached to the body section, the treatment end being formed as a seal; and a pressure sensor configured to sense a pressure exerted by the treatment area on the treatment end of the treatment section, wherein the controller instructs the electromagnetic source to begin projecting only when (1) the light sensor senses the amount of ambient light at the emitting end of the treatment section is below the predefined threshold, and (2) the pressure sensor senses the pressure exerted by the area of the skin on the treatment end of the treatment section is above a predefined pressure.

Example Claim 3: The personal care implement of any of the preceding claims, wherein the controller instructs the electromagnetic source to project only when the light sensor senses the amount of ambient light at the emitting end is below the predefined threshold.

Example Claim 4: The personal care implement of any of claims 2-3, wherein the controller instructs the electromagnetic source to project the electromagnetic radiation only when (1) the light sensor senses the amount of ambient light at the emitting end is below the predefined threshold, and (2) the pressure sensor senses the pressure exerted by the area of the skin on the emitting end is above a predefined pressure.

Example Claim 5: The personal care implement of any of the preceding claims, further comprising a timer, the controller being configured to instruct the electromagnetic source to continue projecting the electromagnetic radiation for a predetermined period of time measured by the timer.

Example Claim 6: The personal care implement of any of the preceding claims, further comprising a movable joint that attaches the treatment section to the body section.

Example Claim 7: The personal care implement of claim 6, wherein the pressure sensor senses a movement of the movable joint.

Example Claim 8: The personal care implement of any of claims 6-7, wherein the movable joint is a telescoping joint.

Example Claim 9: The personal care implement of any of claims 6-8, wherein the movable joint comprises bellows.

Example Claim 10: The personal care implement of any of claims 6-9, wherein the movable joint is a pivoting joint.

Example Claim 11: The personal care implement of any of claims 1-5, wherein the emitting section is fixed relative to the body.

Example Claim 12: The personal care implement of any of the preceding claims, wherein the predetermined threshold of the light sensor is an amount of light present outside of the emitting end.

Example Claim 13: The personal care implement of any of the preceding claims, wherein the emitting end comprises an opening.

Example Claim 14: The personal care implement of claim 13, wherein the electromagnetic radiation projects toward the opening.

Example Claim 15: The personal care implement of any of claims 13-14, wherein the light sensor senses the amount of ambient light at the opening.

Example Claim 16: The personal care implement of any of claims 13-15, wherein the predetermined threshold of the light sensor is an amount of light present outside of the opening.

Example Claim 17: The personal care implement of any of the preceding claims, further comprising an illuminating light source for illuminating the treatment area.

Example Claim 18: The personal care implement of claim 17, wherein the illuminating light source is a light emitting diode.

Example Claim 19: The personal care implement of any of the preceding claims, wherein the electromagnetic source is a laser.

Example Claim 20: The personal care implement of any of claims 2-19, wherein the pressure sensor is a piezoelectric sensor.

Example Claim 21: The personal care implement of any of the preceding claims, wherein the body section is pen-like.

Example Claim 22: The personal care implement of any of the preceding claims, wherein the electromagnetic source comprises a plurality of electromagnetic sources.

Example Claim 23: The personal care implement of claim 22, wherein the plurality of electromagnetic sources are arranged in a ring formation.

Example Claim 24: The personal care implement of any of claims 13-22, wherein the plurality of electromagnetic sources are arranged in a ring formation around the opening.

Example Claim 25: The personal care implement of any of the preceding claims, further comprising a battery unit that provides power to the treatment light source.

Example Claim 26: A method of preventing an electromagnetic source from projecting from a hand-held personal care implement, the method comprising: providing the hand-held personal care implement with an emitting end, an electromagnetic source for projecting electromagnetic radiation onto an area of skin, a light sensor configured to sense an amount of ambient light present at the emitting end, and a controller; and beginning to project the electromagnetic radiation onto the area of skin only when the light sensor of the personal care implement senses the amount of ambient light at the emitting end of the personal care implement is below a predefined threshold.

Example Claim 27: The method of claim 26, further comprising providing the personal care implement with a pressure sensor configured to sense a pressure exerted by the skin on the emitting end; and beginning to project the electromagnetic radiation onto the area of skin only when (1) the light sensor senses the amount of ambient light at the emitting end is below the predefined threshold, and (2) the pressure sensor senses that the pressure exerted by the area of skin on the emitting end is above a predefined pressure.

Example Claim 28: The method of any of claims 26-27, wherein the controller instructs the electromagnetic source to project the electromagnetic radiation only when the light sensor senses that the amount of ambient light at the emitting end is below the predefined threshold.

Example Claim 29: The method of any of claims 26-28, wherein the controller instructs the electromagnetic source to project the electromagnetic radiation only when (1) the light sensor senses that the amount of ambient light at the emitting end is below the predefined threshold, and (2) the pressure sensor senses the pressure exerted by the area of skin on the emitting end is above a predefined pressure.

Example Claim 30: The method of any of claims 26-29, further comprising controlling a duration of continued projection of the electromagnetic source with a timer.

Example Claim 31: The method any of claims 26-30, wherein the personal care implement further comprises a body section; a treatment section including the emitting end and a body end, the emitting end being located at a distal end of the treatment section and opposite the body end, the body end being attached to the body section, the treatment end being formed as a seal, and a movable joint that attaches the treatment section to the body.

Example Claim 32: The method of claim 31, wherein the pressure sensor senses a movement of the movable joint.

Example Claim 33: The method of any of claims 31-32, wherein the movable joint is a telescoping joint.

Example Claim 34: The method of any of claims 31-33, wherein the movable joint comprises bellows.

Example Claim 35: The method of any of claims 31-34, wherein the movable joint is a pivoting joint.

Example Claim 36: The method of any of claims 26-30, wherein the personal care implement further comprises a body section; a treatment section including the emitting end and a body end, the emitting end being located at a distal end of the treatment section and opposite the body end, the body end being attached to the body section, the treatment end being formed as a seal, and the treatment section is fixed relative to the body section.

Example Claim 37: The method of any of claims 26-36, wherein the predetermined threshold of the light sensor is an amount of light present outside of the emitting end.

Example Claim 38: The method of any of claims 26-37, wherein the emitting end comprises an opening in the treatment section.

Example Claim 39: The method of claim 38, wherein the electromagnetic radiation projects toward the opening.

Example Claim 40: The method of any of claims 38-39, wherein the light sensor senses the amount of ambient light at the opening.

Example Claim 41: The method of any of claims 38-40, wherein the predetermined threshold of the light sensor is an amount of light present outside of the opening.

Example Claim 42: The method of any of claims 26-41, further comprising an illuminating light source for illuminating the area of skin.

Example Claim 43: The method of claim 42, wherein the illuminating light source is a light emitting diode.

Example Claim 44: The method of any of claims 26-43, wherein the electromagnetic source is a laser.

Example Claim 45: The method of any of claims 27-44, wherein the pressure sensor is a piezoelectric sensor.

Example Claim 46: The method of any of claims 26-45, wherein the body section is pen-like.

Example Claim 47: The method of any of claims 26-46, wherein the electromagnetic source comprises a plurality of electromagnetic sources.

Example Claim 48: The method of claim 47, wherein the plurality of electromagnetic sources are arranged in a ring formation.

Example Claim 49: The method of any of claims 38-48, wherein the plurality of electromagnetic sources are arranged in a ring formation around the opening.

Example Claim 50: The method of any of claims 26-49, further comprising a battery unit that provides power to the electromagnetic source.

Example Claim 51: A method of treating a skin condition at a treatment area on skin of a user using a hand-held personal care implement, the method comprising: holding the hand-held personal care implement in the hand of the user; moving the personal care implement into contact with the skin of the user; beginning to project a treatment light source of the personal care implement onto the treatment area of the skin only when a light sensor of the personal care implement senses an amount of ambient light at a treatment end of the personal care implement is below a predefined threshold.

Example Claim 52: The method of claim 51, wherein the treatment light source is a laser.

Example Claim 53: A personal care implement comprising: an emitting end; an electromagnetic source; a light sensor configured to sense an amount of ambient light present at the emitting end; and a controller that instructs the electromagnetic source to begin projecting only when the light sensor senses the amount of ambient light at the emitting end is below a predefined threshold.

Example Claim 54: A personal care implement comprising: a body section; a treatment section having a treatment end and a body end, the treatment end being located at a distal end of the treatment section and opposite the body end, the body end being attached to the body, the treatment end being formed as a seal; a treatment light source for projecting treatment light onto a treatment area, the treatment light source having emission characteristics to treat a skin condition; a light sensor configured to sense an amount of ambient light present at the treatment end of the treatment section; and a controller that instructs the treatment light source to be in an off position when the light sensor senses the amount of ambient light at the treatment end of the treatment section is above a predefined threshold.

Example Claim 55: The personal care implement of claim 54, wherein the controller determines the operating condition of the treatment light source by distinguishing ambient light from other light sources.

Example Claim 56: The personal care implement of any of the preceding (apparatus) claims, wherein the ambient light is light that originates from a source other than the personal care implement.

Example Claim 57: The method of any of the preceding (method) claims, wherein the ambient light is light that originates from a source other than the personal care implement.

Example Claim 58: A personal care implement comprising: a body section; a treatment section having a treatment end and a body end, the treatment end being located at a distal end of the treatment section and opposite the body end, the body end being attached to the body, the treatment end being formed as a seal; a treatment light source for projecting treatment light onto a treatment area, the treatment light source having emission characteristics to treat a skin condition; a light sensor configured to sense an amount of electromagnetic radiation at the treatment end of the treatment section; and a controller that instructs the treatment light source to begin projecting the treatment light only when the light sensor senses the amount of electromagnetic radiation at the treatment end of the treatment section is below a predefined threshold.

Section II

The present disclosure may be directed, in one aspect, to a system for monitoring acne, the system including a sensor device comprising an image sensor configured to generate image data for each of a plurality of images of different portions of a user's skin; a position sensor configured to, for each image of the plurality of images, generate corresponding position data indicative of a position of the sensor device when the image data was generated; a processing device configured to receive the image data and the position data for each of the plurality of images; and combine portions of the image data for each of the plurality of images to generate composite image data, the combination of the portions of the image data based on the corresponding position data for each image of the plurality of images; and a user interface configured to display a composite image of the user's skin based on the composite image data, the composite image comprising a skin condition indicator.

In another aspect, a system for monitoring acne includes a sensor device comprising an image sensor configured to generate image data for each of a plurality of images of different portions of a surface when the sensor device is placed at or near the surface; and a position sensor configured to, for each image of the plurality of images, generate corresponding position data indicative of a position of the sensor device when the image data was generated; a processing device configured to receive the image data and the position data for each of the plurality of images; and combine portions of the image data for each of the plurality of images to generate composite image data, the combination based on the corresponding position data for each image of the plurality of images; and a user interface configured to display a composite image of the surface based on the composite image data.

In yet another aspect, a method for monitoring acne includes generating, by an image sensor, image data for each of a plurality of images of different portions of a user's skin; for each image of the plurality of images, generating corresponding position data indicative of a position of the sensor device when the image data was generated; combining portions of the image data for each of the plurality of images to generate composite image data, the combination based on the corresponding position data for each image of the plurality of images; and displaying a composite image of the user's skin based on the composite image data, the composite image comprising a skin condition indicator.

Figure 11:
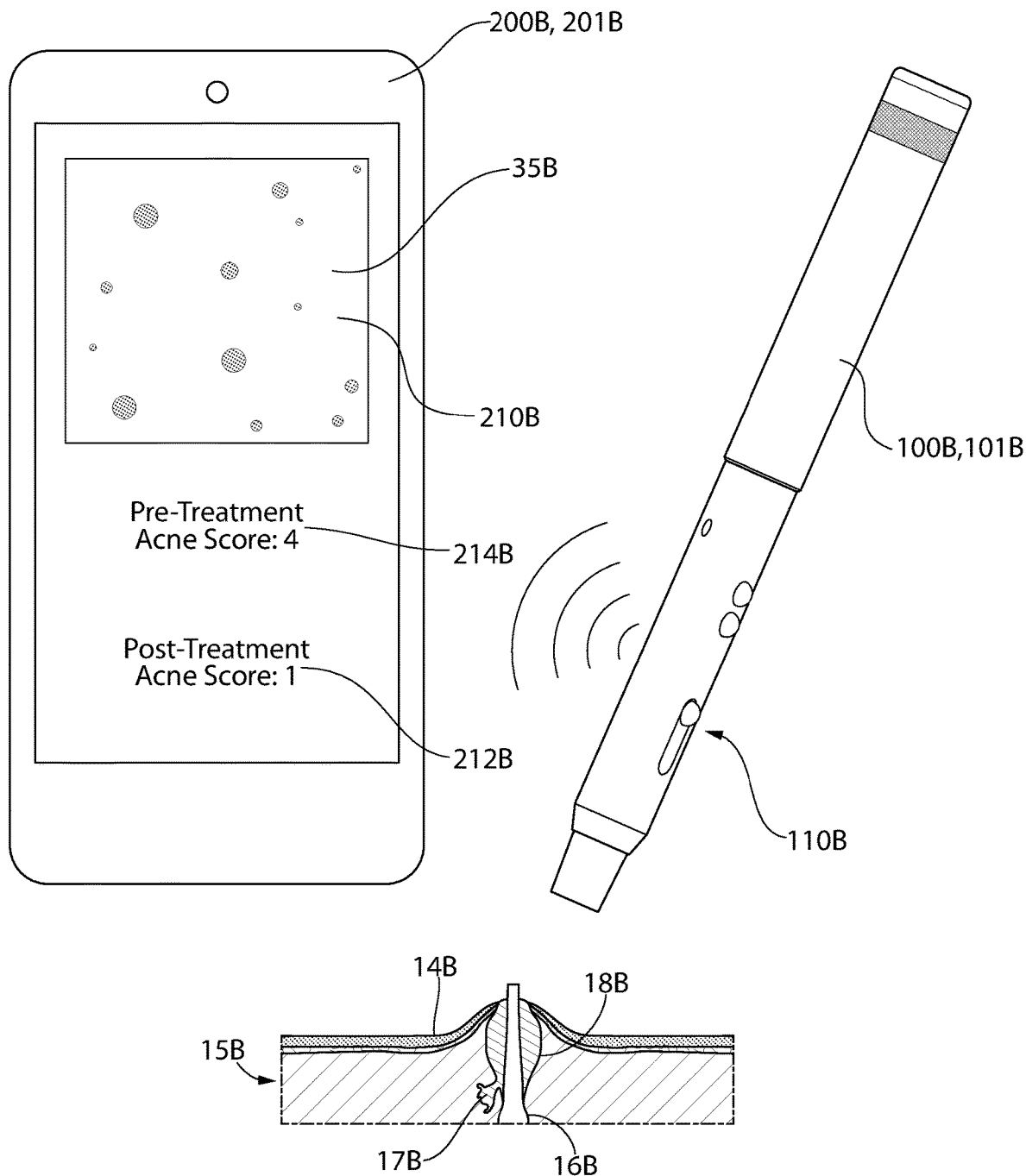
FIG. 11 shows a system for monitoring acne according to one embodiment.

Referring now to the figures, FIG. 11 shows a system 10B for monitoring acne according to one embodiment. The exemplified system 10B includes a sensor device 100B configured to take images of a user's skin 15B, and to transfer image data to a user interface 210B for display of an image 35B of the user's skin 15B. As will be discussed below, the device 100B can image potential acne-prone sites on the skin 15B (such as the skin on the user's face) by targeting the fluorescence emission of porphyrin, the metabolic byproduct of pAcnes (*Propionibacterium acnes*), and transmit data to a processing device 200B to analyze and interpret image data. The exemplified system can thereby act as an early detection system for the consumer to prevent the proliferation of acne. In the exemplified embodiment, the sensor device 100B can take images of the user's skin 15B when the device 100B is at or near (within millimeters) of the skin 15B, though the invention is not so limited. In the exemplified embodiment, the sensor device is a handheld device, though the invention is not so limited. For example, in certain embodiments, the sensor device can be configured to independently move along a surface.

The user interface 210B can display an acne score 214B and a previous acne score 212B indicative of an amount of acne detected from the composite image 35B and an amount of acne detected from a previous composite image, respectively. This process can utilize an algorithm using quantitative analysis to develop an index. In the exemplified embodiment, the algorithm calculates the sum of intensity of spot brightness multiplied by the spot size across the entire set of images measured. This enables the user to receive an acne score indicative of the extent of the acne present in the imaged portion of the user's skin, and to compare this with previous scores to determine how effective a treatment has been. In other embodiments, other methods of image recognition and processing can be utilized.

The exemplified system includes a processing device 200B. The processing device 200B can be any device configured to process image data from the sensor device 100B. The processing device 200B can form part of the sensor device 100B or, as in the current embodiment, be a separate device, such as a portable electronic device (e.g., a smartphone, tablet, or laptop) or a stationary device (e.g., a desktop computer). In the exemplified embodiment, the processing device is a smartphone enclosed by a housing 201B separate from a housing 101B of the sensor device 100B. In other embodiments, the processing device 200B and the sensor device 100B can share the same housing. For example, both devices 100B, 200B can form part of a smartphone. The system can also include a remote server (not shown) in communication with the processing device and/or the device 100B, and at which one or more of the processing steps discussed herein can be carried out.

The exemplified processing device 200B further includes a user interface 210B for displaying the image 35B of the user's skin 15B. In other embodiments, this user interface can form part of a different device, such as the sensor device 100B. As used herein, the term "user interface" can refer to any component or apparatus by which a person interacts with a corresponding device. For example, a user interface can be a screen, a touch screen, a mouse, a keyboard, a button, a switch, an LED display, or any combination thereof. A user interface can provide output, input, or both.

The exemplified sensor device 100B includes its own user interface 110B. In the exemplified embodiment, this handheld user interface 110B includes controls for turning the sensor device 100B ON and OFF, thus enabling or disabling its ability to capture images of the surface 14B of the user's skin. In other embodiments, the user interface 110B can include other standard features, such as lights indicating whether the device 100B is on, controls determining the time that images will be captured, controls determining the strength of a light provided by the device 100B, or a display for showing information such as an image of the user's face similar to image 35B.

As shown in the cross-sectional view of a user's skin 15B, the sebaceous glands 17B of the user's skin 15B produce sebum, a mixture of lipids composed mainly of triglycerides (TG), wax esters (WE), squalene, free fatty acids (FFA) and smaller amounts of cholesterol, cholesterol esters (ChoE) and diglycerides. Sebum coats the hair and skin surface following a holocrine secretion into the infundibulum of the hair follicle 16B. The follicular impactions develop into initially invisible lesions (microcomedones) and then into clinically evident comedones. Microcomedones and comedones are a suitable microenvironment for colonization by cutaneous bacteria 18B, especially *Propionibacterium acnes*.

These bacteria 18B produce proinflammatory mediators and free fatty acids, which are responsible for the appearance of inflamed acne lesions (papules, pustules and nodules). Porphyrins (protoporphyrin, coproporphyrin I and mainly coproporphyrin III) are further endogenous metabolic products of *Propionibacterium* 18B, which might additionally contribute to the perifollicular inflammatory reaction. Porphyrins are native fluorophores that emit strong fluorescence when exposed to light of the right frequency (340 nm-450 nm). Their presence can be demonstrated by detection of an orange-red fluorescence in the openings of the follicle 16B by examining facial skin with appropriate visible range detectors typically in the 500-700 nm range.

Figure 12:
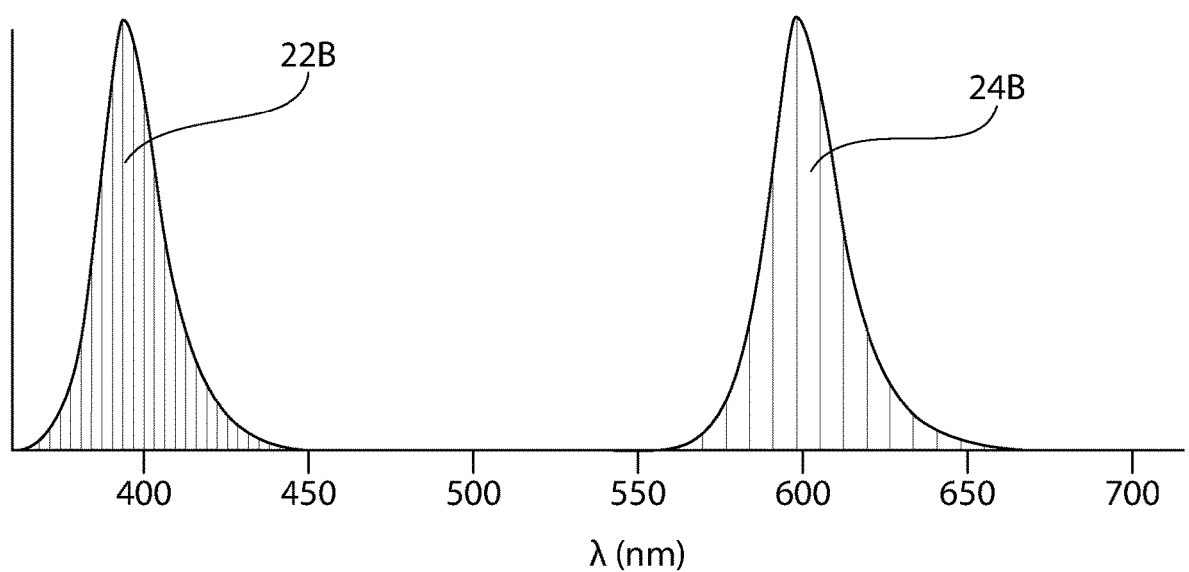
FIG. 12 is a graph of excitation and emission spectra of porphyrin.
Figure 13A:
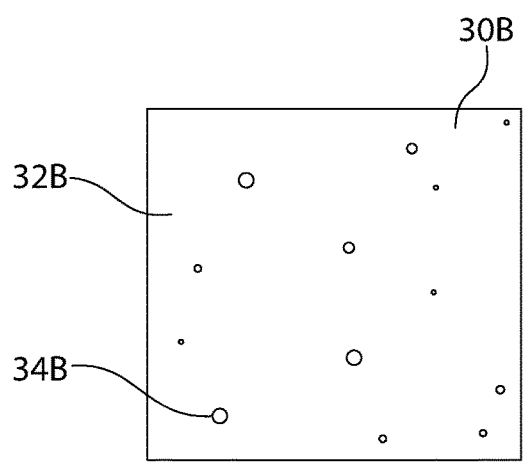
FIG. 13A is a raw composite RGB image of a user's face according to one embodiment.
Figure 13B:
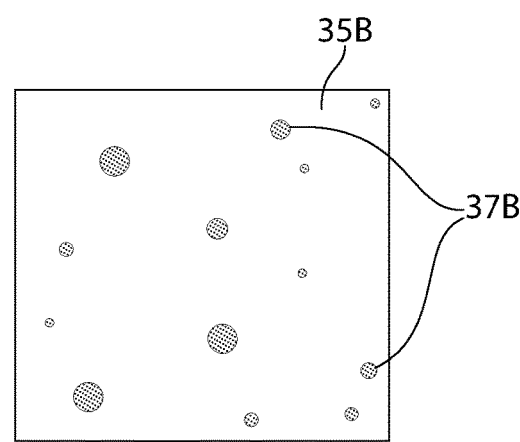
FIG. 13B is a processed spectrally unmixed composite image of a user's face according to one embodiment.
Figure 14:
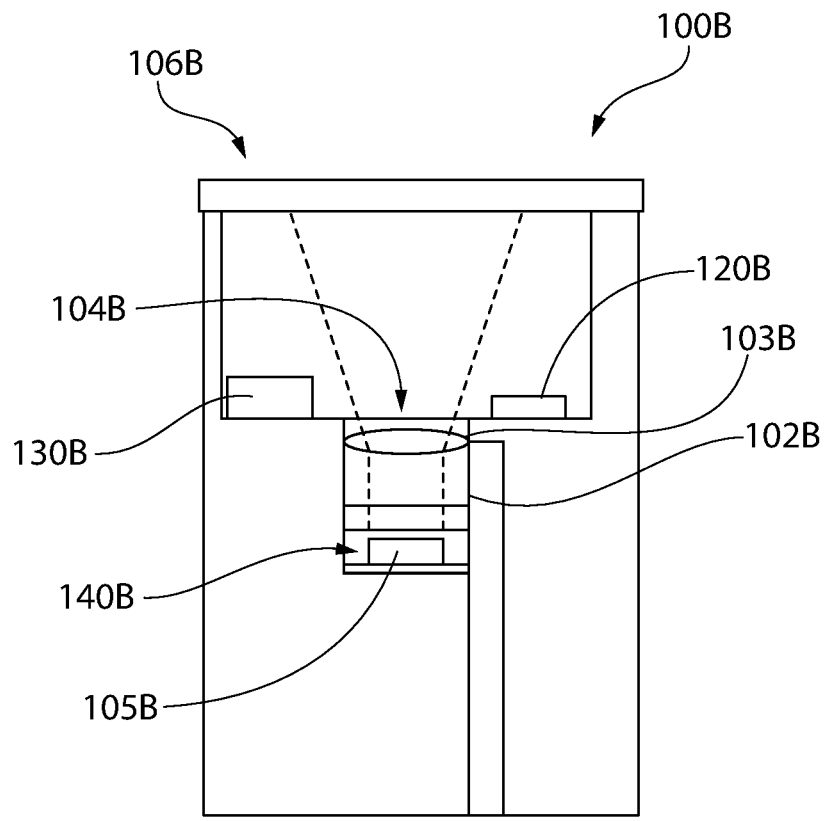
FIG. 14 is a side view block diagram of a first end of the sensor device according to one embodiment.

FIG. 12 is a graph 20B showing the excitation and emission spectra 22B, 24B of porphyrin. As can be seen, the excitation spectra range from approximately 340 nm-450 nm. Thus, porphyrins can emit fluorescence when exposed to light of this frequency. By contrast, the emission spectra range from approximately 550-675 nm. Thus, porphyrin fluorescence emission will likely be in this range.

In other embodiments, other indicators of acne can be used to detect and monitor acne. For example, a different byproduct or indicator of acne can be responsive to a certain range of light. In other embodiments, other methods for identifying acne can be utilized, such as those not utilizing fluorescence or light.

FIG. 3A is a raw composite RGB image 30B of a portion of a user's face according to one embodiment. The process for generating this composite image is discussed in greater detail below. The orange-red spots 34B are due to the emission fluorescence of porphyrin byproducts produced by the pAcnes bacteria 18B. The orange-red spots thus are acne indicators 34B. The green portion 32B shows the light reflected by the areas of skin without acne.

FIG. 3B shows a processed spectrally unmixed composite image 35B of a user's face, which includes processed acne indicators 37B. To create this image 35B, composite image data for the composite image 30B can be processed. The processing can enable a user to more easily view the acne indicators or spots 37B. In the exemplified embodiment, the colors of the background and the indicators 37B are altered to enhance the contrast and improve visibility of the indicators 37B. Standard image processing methods can be used to improve the visibility of the acne indicators 37B.

It is noted that, while the exemplified embodiment displays a composite image comprising acne indicators, the invention is not limited to the display of acne indicators. In other embodiments, other skin condition indicators can be monitored and displayed. For example, the invention can be used to perform mole mapping for monitoring skin cancer. Further, other skin irregularities or visual conditions can be monitored, such as redness, swelling, or a skin reaction to a treatment regimen. The skin condition indicators can be indicative of any type of condition and/or irregularity visible on the skin. In yet other embodiments, a skin condition indicator can be omitted from the display.

FIG. 4 is a side view block diagram of a first end 106B of the sensor device 100B according to one embodiment. The device includes a light source 120B configured to illuminate a surface. In this embodiment, the surface is a portion of the user's face, though the invention is not so limited. In other embodiments, the surface can be any skin surface (human, animal, or otherwise), including surfaces of the back, chest, oral tissues, and/or mucous membranes. In yet other embodiments, the surface can be any type of surface, including a non-skin or non-biological surface. The light source 120B can provide any type of light. In the exemplified embodiment, the light source 120B comprises light-emitting diodes (LEDs) driven by a current source and controlled by a microcontroller (see FIG. 15) of the device 100B. In this embodiment, the light source 120B is configured to generate one or more excitation wavelengths effective to cause at least one of the plurality of images to include an acne indicator indicating the presence of porphyrin, the metabolic byproduct of *Propionibacterium acnes*, in the user's face. The excitation wavelengths can be configured to cause the porphyrin in the user's face to emit orange or red fluorescence in follicle openings.

In the exemplified embodiment, the excitation wavelengths are 405 nm (blue). But as discussed above, in other embodiments, the excitation wavelengths can be other values, such as between 390 and 420 nanometers. In other embodiments, a photosensitizer may be used on the skin such that a different wavelength (e.g., 630 nm) is effective. In yet other embodiments, the light source can be omitted and an image sensor can capture images without the aid of a light source.

An image sensor 160B can be configured to generate image data for each of a plurality of images of different portions of a user's face. In the exemplified embodiment, the images are small in the amount of surface area they capture due to the small size and pen-like shape of the handheld sensor device. Thus, the individual images are smaller than the overall area of skin that is of concern. Thus, in the exemplified embodiment, the image data from each individual image is combined to create a composite image of the user's skin or a portion thereof.

In the exemplified embodiment, the image sensor 160B is configured to capture orange or red fluorescence in at least one of the plurality of images, this fluorescence being an acne indicator. Further, the emission may be band-passed filtered to eliminate unwanted excitation light. In the exemplified embodiment, the image sensor is a charge-coupled device (CCD) image sensor using CMOS technology. The image sensor is discussed in greater detail below.

The exemplified sensor device 100B includes a lens barrel 102B, lens 103B, and aperture 104B to assist the image sensor 160B in capturing images. Further, a dichroic (long pass) filter 105B can be used for selectively passing light of a small range of colors while reflecting others. The lens can use traditional manual focus tuning, or be an electrically tunable lens based on shape-changing elastic polymer material or electrowetting-driven liquid lens technology.

The exemplified device 100B further includes a position sensor 130B configured to, for each image of the plurality of images, generate corresponding position data indicative of a position of the sensor device 100B when the image data was generated. This sensor 130B is discussed in greater detail below.

For purposes of the present disclosure, the term "image data" is any type of information indicative of an image, including information extracted or derived from other information or data indicative of an image, regardless of the form of the extracted information, and combinations thereof. The image data may be in the form of mathematical data, analog data, and/or digital data.

Figure 15:
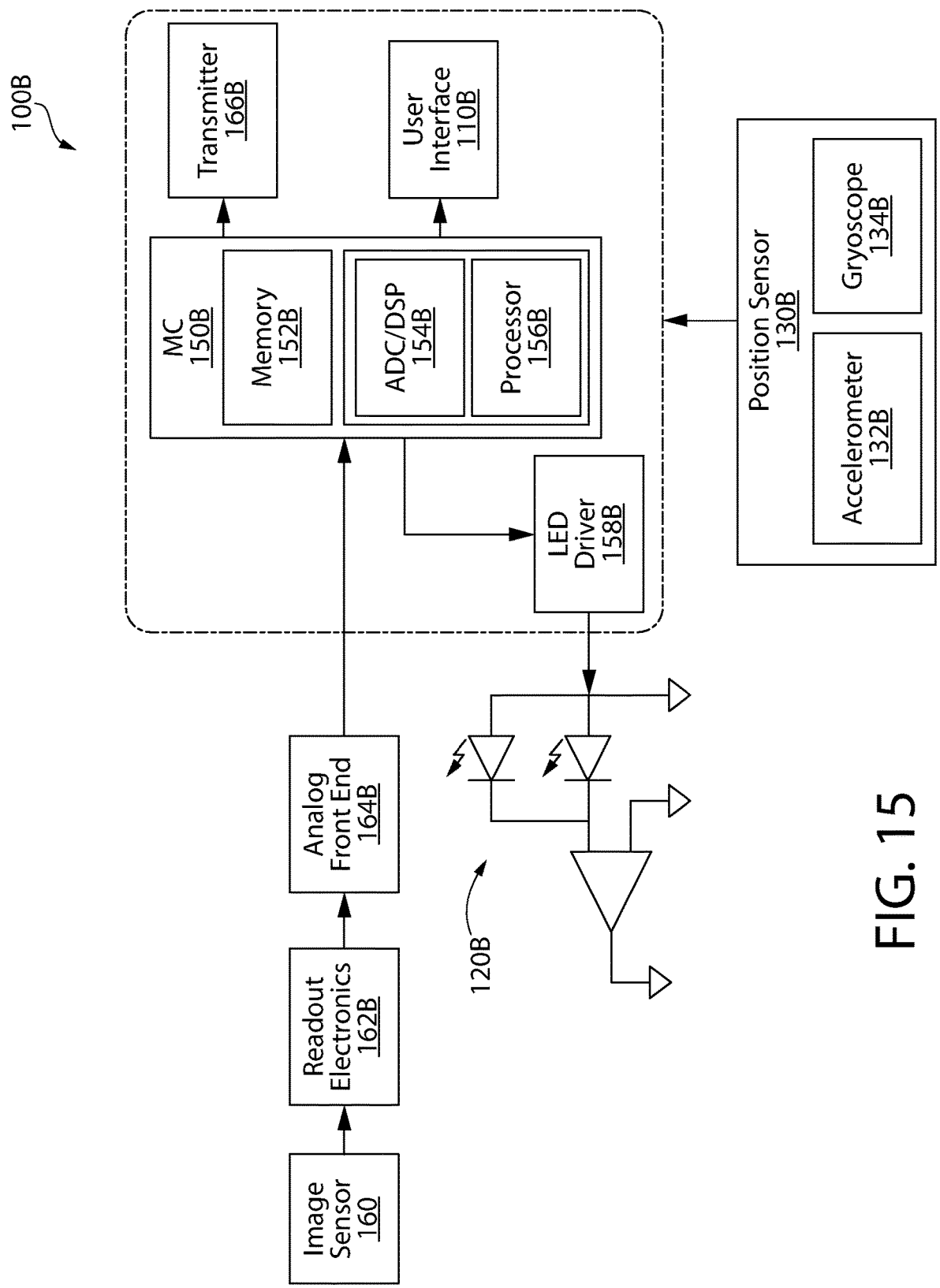
FIG. 15 is a block diagram of the sensor device according to one embodiment.

FIG. 15 is a block diagram of the sensor device 100B according to one embodiment. The exemplified device 100B includes an image sensor 160B, as well as readout electronics 162B for transferring the image data from the image sensor to an analog front-end system 164B.

A microcontroller 150B is operably coupled to the image sensor 160B. The microcontroller 150B includes a memory 152B, an analog-to-digital converter (ADC) and digital signal processor (DSP) 154B, and the processor 156B. The processor 156B is operably coupled to the image sensor 160B and the position sensor 130B, and is configured to control the image sensor 160B. For example, the processor 156B can instruct the image sensor 160B to begin collecting image data.

The exemplified microcontroller 150B and processor 156B are operably coupled to the sensor device user interface 110B discussed above. Further, the microcontroller 150B and processor 156B are operably coupled to a transmitter 166B for transmitting the image data and the position data. In the exemplified embodiment, the transmitter 166B includes an RF circuit and an antenna and is configured to transmit the image data and the position data to the processing device by wireless RF signals.

The exemplified microcontroller 150B and processor 156B are also operably coupled to a light source 120B for illuminating a surface and a driver 158B for controlling the light source 120B. In the exemplified embodiment, the light source 120B is one or more LEDs and the driver is an LED driver. In other embodiments, the light source can provide any type of illumination.

The exemplified device 100B further includes a position sensor 130B configured to, for each image of the plurality of images, generate corresponding position data indicative of a position of the sensor device 100B when the image data was generated. As used herein, the term "position data" can refer to any type of information indicative of a position of the sensor device or a component of the sensor device, including information extracted or derived from other information or data indicative of a position, regardless of the form of the extracted information, and combinations thereof. The position data may be in the form of mathematical data, analog data, and/or digital data. For example, the position data can be indicative of a spatial orientation of the sensor device and/or a motion of the sensor device. The position data can also be related to other factors, such as acceleration, velocity, or proximity to a reference point (such as a marker of a feature of the user's skin).

The processing device 200B can be configured to receive the image data and the position data for each of the plurality of images. Further, the processing device 200B can be configured to combine portions of the image data for each of the plurality of images to generate composite image data, and the composite image data can be used to generate a composite image of the user's skin. For example, the composite image data can convert small images of the user's face into a composite image of a portion (or an entirety) of the user's face. The combination of the image data can be based on the corresponding position data for each image of the plurality of images, thereby enabling the separate images from the sensor device to be aligned and stitched together. The composite image can include the acne indicators (see FIG. 11), thus providing the user a view of where acne is developing on his or her face.

The composite image data can be generated by several different means. For example, the composite image data can be generated by extracting the relative displacement of each of the plurality of images during movement of the sensor device along the user's face. Further, as discussed above, the composite image data can be processed such that the composite image comprises colors that allow the acne indicator to be more easily viewed.

In the exemplified embodiment of FIG. 15, the position sensor 130B comprises an accelerometer 132B and a three-axis gyroscope 134B for tracking the position of each of the plurality of images. This information can be used to determine how to combine the images into a composite image. In the exemplified embodiment, the images will have overlapping portions, though the invention is not so limited. Any type of image stitching method or other method for combining images into a composite image can be utilized.

Figure 16:
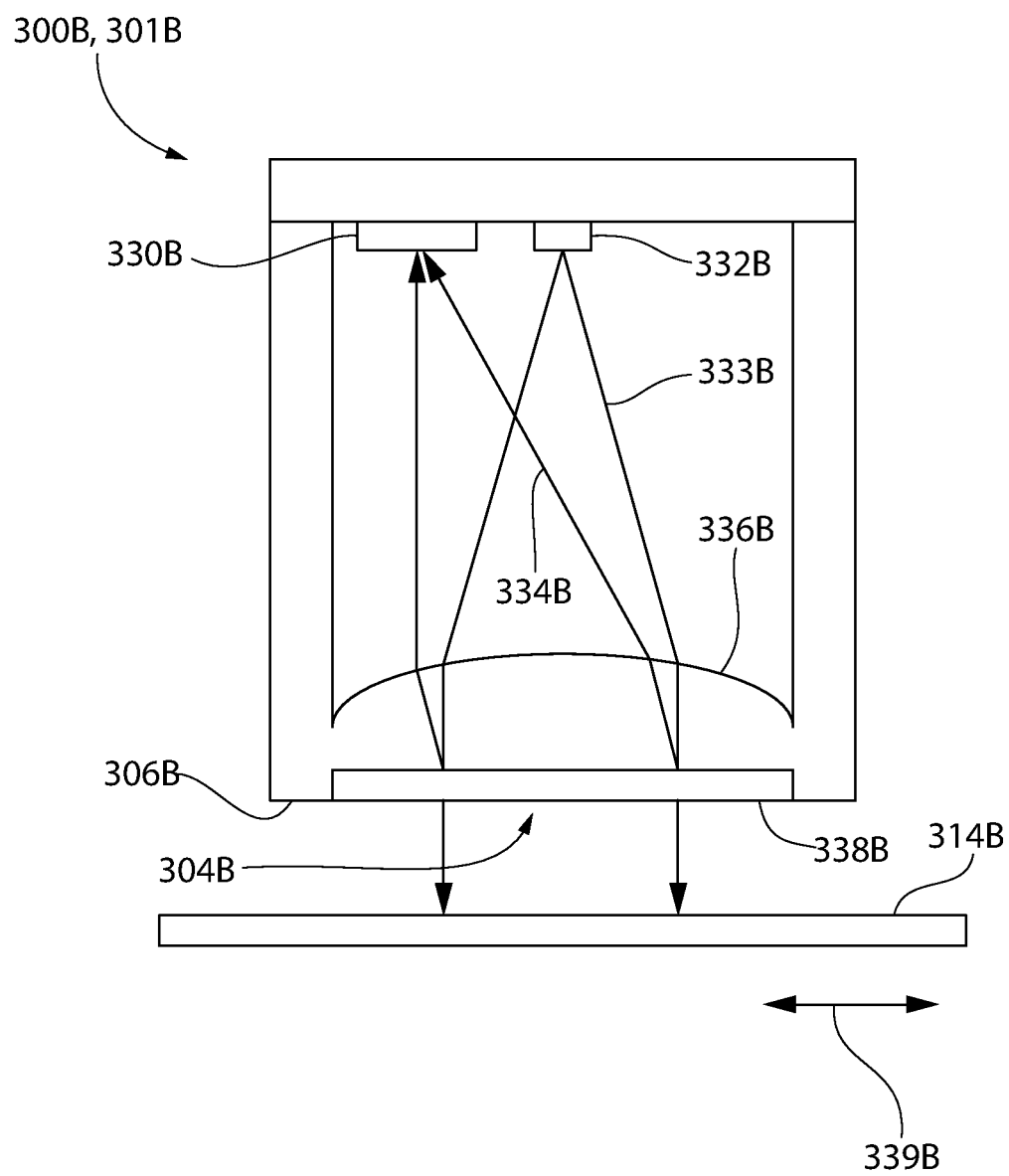
FIG. 16 is a side block diagram of a first end of a sensor device having a position sensor utilizing optical translation measurement (OTM) technology according to one embodiment.

FIG. 16 is a side block diagram of a first end 306B of a sensor device 301B having a position sensor 330B forming part of an optical translation measurement (OTM) assembly 301B. The assembly 301B can be used to determine the relative transverse motion 339B of the device 301B when the aperture 304B of the device is placed adjacent (on or within millimeter) and moved along a surface of the user's skin 314B. The relative transverse motion 339B can be used to detect where the images were taken, and thus how the images can be combined to create a composite image.

OTM technology uses diffusive (non-specular) reflected light. OTM is characterized by high signal-to-noise ratio (SNR), high accuracy, resolution of a few wavelengths, and insensitivity of the measurement to the distance to and the type of the surface. OTM is typically integrated into a small, transistor-style package, using a solid-state laser and molded plastic optics. The OTM assembly 301B requires low power, and can be mass-produced at a low unit cost. OTM technologies such as that offered by OTM Technologies Ltd. can be incorporated into the sensor device 300B for position sensing.

The exemplified device 300B includes a position laser 332B emitting an illumination 333B, a collimation lens and a focusing lens 336B, a grating 338B, a position sensor 330B (e.g., a detector), an aperture 304B, and signal conditioning electronics (not shown). The functions of the collimation lens 336B, grating 338B, and focusing lens 336B into a single integrated optical element. The position laser 332B provides coherent light that is collimated by the collimation lens 336B and directed towards the surface of the user's skin 314B. The optical grating 338B is placed between the position laser 332B and the surface 314B, and serves as a partial reflector to provide local oscillator 334B beams. The light reflected from the surface 314B and the light that is reflected from the grating 338B are both focused onto the position sensor 330B by the focusing lens 336B, such that each position sensor 330B measures a single reflected local oscillator beam.

In one embodiment, the optical translation measurements are used to determine position data indicative of a position and a velocity of the sensor device. Further, the measurements are made by using the reflected light to measure the relative motion of the surface of the user's skin 314B when the aperture 304B of the sensor device 300B is placed substantially adjacent to the surface of the user's skin 314B.

A method of monitoring acne can be considered to include the following steps: generating, by an image sensor, image data for each of a plurality of images of different portions of a user's skin; for each image of the plurality of images, generating corresponding position data indicative of a position of the sensor device when the image data was generated; combining portions of the image data for each of the plurality of images to generate composite image data, the combination based on the corresponding position data for each image of the plurality of images; and displaying a composite image of the user's skin based on the composite image data, the composite image comprising an acne indicator.

While the embodiments discussed above discuss a system and method for monitoring acne, the invention is not so limited. For example, in another embodiment, the system can comprise a sensor device whose image sensor is configured to generate image data for different portions of a surface when the sensor device is place at or near the surface being imaged. The composite image can be based on image data and position data, and the composite image can be used to identify a different feature of a skin surface (e.g., indicators on the skin of an abnormality, such as welts, blisters, lesions, or bruises), to identify a feature of another type of surface, or simply to create a composite image.

The embodiments discussed herein address, among other things, the need for a low-cost, at-home imaging device and method for the early detection and monitoring of acne, including providing early prediction of potential acne breakout locations on the skin. These embodiments offer methods to determine, among other things, how well the face is being washed and how well treatment methods are working without the inconvenience of visiting a dermatologist's office. The embodiments also discuss methods for creating a composite image of a surface based on images taken by a sensor device positioned near the surface.

Example Claims

Example Claim 1: A system for monitoring acne, the system comprising: a sensor device comprising: an image sensor configured to generate image data for each of a plurality of images of different portions of a user's skin; and a position sensor configured to, for each image of the plurality of images, generate corresponding position data indicative of a position of the sensor device when the image data was generated; a processing device configured to: receive the image data and the position data for each of the plurality of images; and combine portions of the image data for each of the plurality of images to generate composite image data, the combination of the portions of the image data based on the corresponding position data for each image of the plurality of images; and a user interface configured to display a composite image of the user's skin based on the composite image data, the composite image comprising a skin condition indicator.

Example Claim 2: The system of any of the preceding claims wherein the plurality of images comprises images of the user's face taken at or near the surface of the user's face.

Example Claim 3: The system of any of the preceding claims wherein the sensor device is a handheld device.

Example Claim 4: The system of any of the preceding claims wherein the skin condition indicator is an acne indicator.

Example Claim 5: The system of any of the preceding claims wherein the processing device is enclosed by a housing separate from a housing of the sensor device.

Example Claim 6: The system of any of the preceding claims wherein the composite image data is generated by extracting the relative displacement of each of the plurality of images during movement of the sensor device along the user's skin.

Example Claim 7: The system of any of the preceding claims wherein the composite image is based on an alignment of the plurality of images.

Example Claim 8: The system of any of the preceding claims wherein the processing device processes the composite image data such that the composite image comprises altered colors that allow the skin condition indicator to be more easily viewed.

Example Claim 9: The system of any of the preceding claims further comprising a light source configured to illuminate a portion of the user's skin.

Example Claim 10: The system of claim 9 wherein the skin condition indicator is an acne indicator, and the light source is configured to generate one or more excitation wavelengths effective to cause at least one of the plurality of images to include the acne indicator indicating the presence of porphyrin in the user's skin.

Example Claim 11: The system of claim 10 wherein the excitation wavelengths are between 390 and 420 nanometers.

Example Claim 12: The system of claim 11 wherein: the excitation wavelengths are configured to cause the porphyrin in the user's skin to emit orange or red fluorescence in follicle openings; and the image sensor is configured to capture the orange or red fluorescence in at least one of the plurality of images as the acne indicator.

Example Claim 13: The system of claim 12 wherein the light source comprises LEDs controlled by a microcontroller of the sensor device.

Example Claim 14: The system of any of the preceding claims wherein the user interface forms part of the processing device.

Example Claim 15: The system of any of the preceding claims wherein the user interface displays an acne score indicative of an amount of acne detected from the composite image.

Example Claim 16: The system of claim 15 wherein the user interface displays a previous acne score indicative of an amount of acne detected from a previous composite image.

Example Claim 17: The system of any of the preceding claims wherein the position data is indicative of a spatial orientation of the sensor device.

Example Claim 18: The system of any of the preceding claims wherein the position data is indicative of a motion of the sensor device.

Example Claim 19: The system of any of the preceding claims wherein the position sensor comprises an accelerometer and a three-axis gyroscope for tracking the position of each of the plurality of images.

Example Claim 20: The system of any of the preceding claims wherein the position sensor is configured to make optical translation measurements to determine the position data, the position data indicative of a position and a velocity of the sensor device.

Example Claim 21: The system of claim 20 wherein the position sensor is configured make optical translation measurements by using reflected light to measure the relative motion of a surface of the user's skin when an aperture of the sensor device is placed substantially adjacent to the surface of the user's skin.

Example Claim 22: The system of claim 21 wherein the reflected light is diffusive and non-specular.

Example Claim 23: The system of any of the preceding claims wherein the image sensor is a charge-coupled device.

Example Claim 24: The system of any of the preceding claims wherein the sensor device further comprises a dichroic filter.

Example Claim 25: The system of any of the preceding claims wherein sensor device further comprises a transmitter configured to transmit the image data and the position data to the processing device by at least one wireless RF signal.

Example Claim 26: The system of any of the preceding claims wherein the sensor device further comprises a processor operably coupled to the image sensor and the position sensor and configured to control the image sensor.

Example Claim 27: The system of claim 26 wherein the sensor device comprising a microcontroller, the microcontroller comprising a memory, an analog-to-digital converter, a digital signal processor, and the processor.

Example Claim 28: The system of claim 27 wherein the sensor device further comprises a sensor device user interface.

Example Claim 29: A system comprising: a sensor device comprising: an image sensor configured to generate image data for each of a plurality of images of different portions of a surface when the sensor device is placed at or near the surface; and a position sensor configured to, for each image of the plurality of images, generate corresponding position data indicative of a position of the sensor device when the image data was generated; a processing device configured to: receive the image data and the position data for each of the plurality of images; and combine portions of the image data for each of the plurality of images to generate composite image data, the combination based on the corresponding position data for each image of the plurality of images; and a user interface configured to display a composite image of the surface based on the composite image data.

Example Claim 30: A method for monitoring acne, the method comprising: generating, by an image sensor, image data for each of a plurality of images of different portions of a user's skin; for each image of the plurality of images, generating corresponding position data indicative of a position of the sensor device when the image data was generated; combining portions of the image data for each of the plurality of images to generate composite image data, the combination based on the corresponding position data for each image of the plurality of images; and displaying a composite image of the user's skin based on the composite image data, the composite image comprising a skin condition indicator.

Example Claim 31: The method of claim 30 wherein the plurality of images comprises images of the user's face taken at or near the surface of the user's face.

Example Claim 32: The method of any of claim 30-31 wherein device is a handheld device.

Example Claim 33: The method of any of claim 30-32 wherein the skin condition indicator is an acne indicator.

Example Claim 34: The method of any of claims 30-33 wherein the composite image data is generated by extracting the relative displacement of each of the plurality of images during movement of the sensor device along the user's skin.

Example Claim 35: The method of any of claims 30-34 wherein the skin condition indicator being an acne indicator, a light source is configured to generate one or more excitation wavelengths effective to cause at least one of the plurality of images to include the acne indicator indicating the presence of porphyrin in the user's skin.

Example Claim 36: The method of any of claims 30-35 further comprising displaying an acne score indicative of an amount of acne detected from the composite image.

Section III

The present disclosure may be directed, in one aspect, to a skin care system comprising a sensor device configured to generate image data for each of a plurality of images of a user's skin, the plurality of images taken at different times; and a processing device configured to receive the image data; determine a change in the image data for the different times; and determine a skin treatment routine or a skin evaluation based on the change in the image data.

In another aspect, a skin care method includes generating, by a sensor device, image data for each of a plurality of images of a user's skin, the plurality of images taken at different times; receiving the image data at a processing device; determining a change in the image data for the different times; and determining a skin treatment routine or a skin evaluation based on the change in the image data.

In another aspect, a skin care system includes a treatment device configured to treat a skin condition, the treatment device comprising a position sensor configured to generate position data indicative of a position of the treatment device; and a processing device configured to receive the position data from the treatment device; and determine a skin treatment session evaluation for a skin treatment session based on the position data for the treatment device.

In another aspect, a skin care method includes activating a treatment device configured to treat a skin condition, the treatment device comprising a position sensor; generating, by the position sensor, position data indicative of a position of the treatment device; receiving, at a processing device, position data from the treatment device; and determining a skin treatment session evaluation for a skin treatment session based on the position data for the treatment device.

In another aspect, a skin care system includes a sensor device configured to generate image data for each of a plurality of images of a user's skin, the plurality of images taken at different times; and a processing device configured to normalize the image data; and determine a skin treatment routine or a skin evaluation based on the normalized image data.

Figure 17:
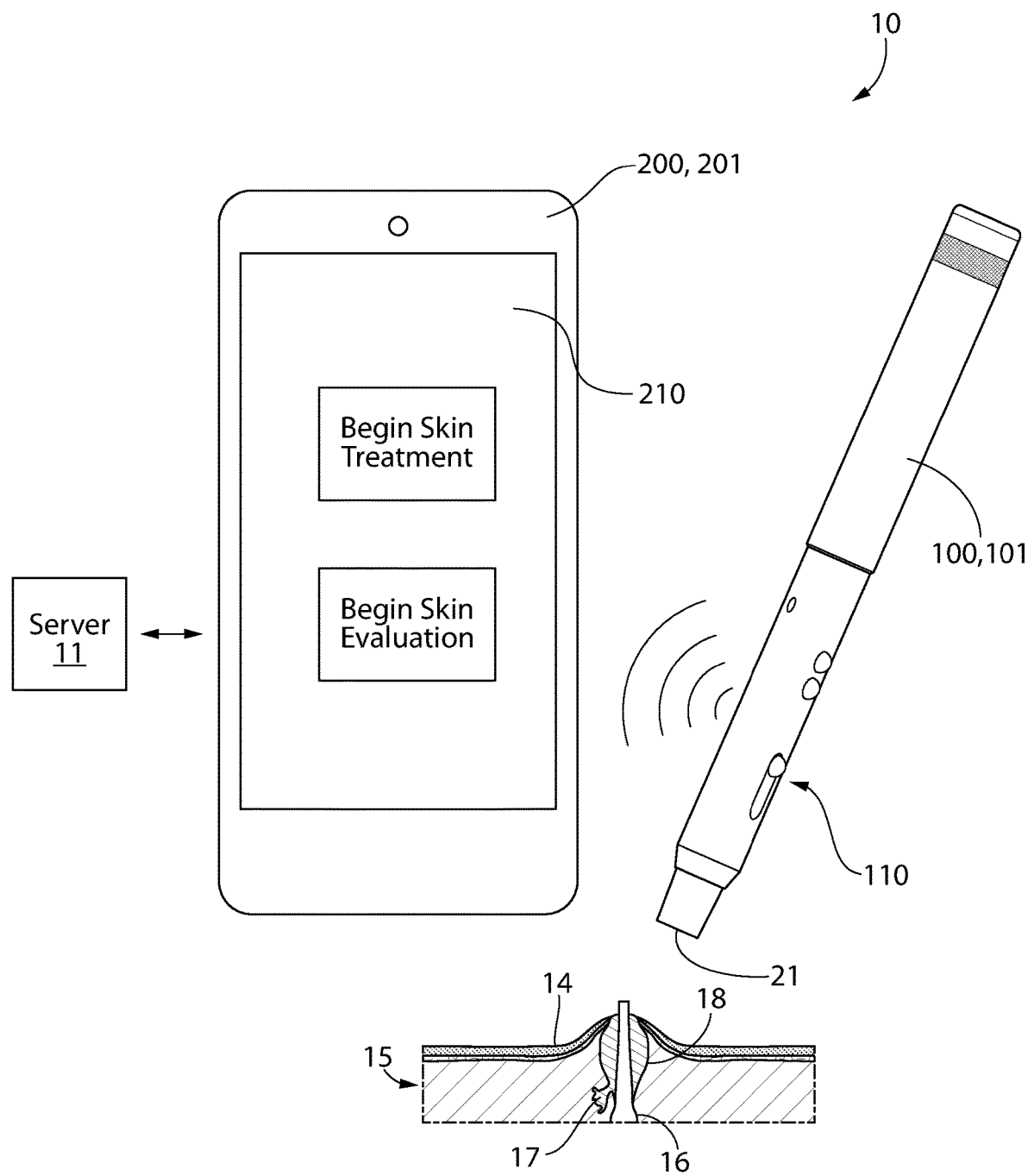
FIG. 17 shows a system for treating and/or evaluating a skin condition according to one embodiment.

Referring now to the figures, FIG. 17 shows a system 10 for treating and/or evaluating a skin condition according to one embodiment. The exemplified system 10 includes a sensor device 100 configured to take images of a user's skin 15 (or otherwise obtain image data), and to transfer image data to a processing device 200 (and/or a server 11) for processing of the image data. In one embodiment, the device 100 can image potential acne-prone sites on the skin 15 (such as the skin on the user's face) by targeting the fluorescence emission of porphyrin, the metabolic byproduct of pAcnes (*Propionibacterium acnes*), and transmit image data to the processing device 200 to analyze and interpret the image data. The exemplified system can thereby act to prevent the proliferation of acne. The disclosure, however, is not so limited, as the system can be used to monitor other skin conditions. For example, the system can be used to perform mole mapping for monitoring skin cancer. Further, other skin irregularities or visual conditions can be monitored, such as redness, swelling, welts, blister, lesions, bruises, or a skin reaction to a treatment regimen.

FIG. 17 includes a cross-sectional view of a user's skin 15, the skin 15 having a skin condition, specifically, an acne growth. The sebaceous glands 17 of the user's skin 15 produce sebum, a mixture of lipids composed mainly of triglycerides (TG), wax esters (WE), squalene, free fatty acids (FFA) and smaller amounts of cholesterol, cholesterol esters (ChoE) and diglycerides. Sebum coats the hair and skin surface following a holocrine secretion into the infundibulum of the hair follicle 16. The follicular impactions develop into initially invisible lesions (microcomedones) and then into clinically evident comedones. Microcomedones and comedones are a suitable microenvironment for colonization by cutaneous bacteria 18, especially *Propionibacterium acnes*.

These bacteria 18 produce proinflammatory mediators and free fatty acids, which are responsible for the appearance of inflamed acne lesions (papules, pustules and nodules). Porphyrins (protoporphyrin, coproporphyrin I and mainly coproporphyrin III) are further endogenous metabolic products of *Propionibacterium* 18, which might additionally contribute to the perifollicular inflammatory reaction. Porphyrins are native fluorophores that emit strong fluorescence when exposed to light of the right frequency (e.g., 340 nm-450 nm). Their presence can be demonstrated by detection of an orange-red fluorescence in the openings of the follicle 16 by examining skin with appropriate visible range detectors typically in the 500-700 nm range.

Figure 26:
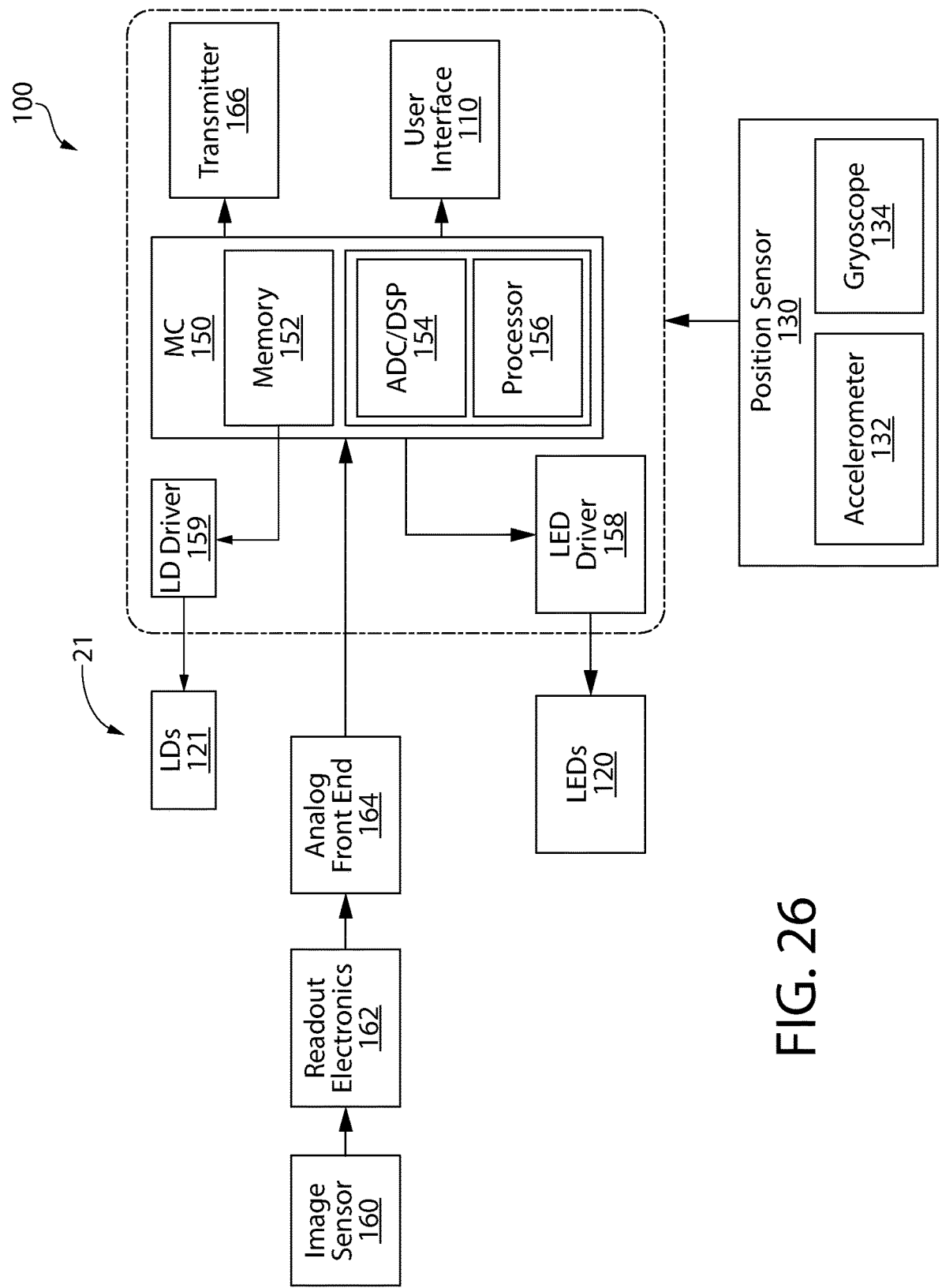
FIG. 26 shows a block diagram of the sensor device according to one embodiment.

Thus, the sensor device 100 can include a light source for illuminating the skin 15 and enabling the capture of the orange-red fluorescence indicative of acne. In one embodiment, this light source can comprise light emitting diodes (LEDs) 120, as shown in FIG. 26. In other embodiments, other light sources can be used for identifying other skin conditions. In yet other embodiments, such a light source can be omitted.

In the exemplified embodiment, the sensor device 100 is a handheld device that can take images of the user's skin 15 when the device 100 is at or near the skin 15, and image data from these images can be stitched together to create a composite image. The disclosure, however, is not so limited. The sensor device can be any device configured to generate image data. For example, the sensor device can be configured take a single image of the relevant user skin, as opposed to stitching together several images. Further, rather than being handheld, the sensor device can be, for example, stationary, or configured to independently move along a surface. Further, while in the exemplified embodiment the sensor device takes images of a human's skin, in other embodiments, the skin can be any skin (human, animal, or otherwise), including skin of the back, chest, oral tissues, and/or mucous membranes.

The processing device 200 can be any device configured to process image data from the sensor device 100. The processing device 200 can form part of the sensor device 100 or, as in the current embodiment, be a separate device, such as a portable electronic device (e.g., a smartphone, tablet, or laptop) or a stationary device (e.g., a desktop computer). In the exemplified embodiment, the processing device is a smartphone enclosed by a housing 201 separate from a housing 101 of the sensor device 100, the processing device 200 in wireless (e.g., Bluetooth) communication with the processing device 200. In other embodiments, the processing device 200 and the sensor device 100 can share the same housing. For example, both devices 100, 200 can form part of a smartphone, where the smartphone camera is used to capture image data. In yet other embodiments, the devices 100, 200 can be separate, but in wired communication.

The exemplified processing device 200 can be in communication with a server 11. Such communication can be carried out by standard means, including Wi-Fi, cellular, and/or internet communication. In other embodiments, the sensor device 100 can be in direct communication with the server. In certain embodiments, the server 11 can be a web server, thereby enabling access to the image data or related data through the internet. For example, using a web server, a dermatologist or other doctor could have ongoing access to some portion of the data relating to the monitoring of the skin condition. The web server could also enable communications between a doctor and patient.

The processing device includes a user interface 210. In FIG. 17, the user interface 210 displays options for beginning a skin treatment and beginning a skin evaluation. As will be shown in subsequent figures, the user interface 210 can provide the user various information and options. For example, the user interface 210 can show a skin treatment routine, a skin evaluation, a skin treatment session evaluation, statuses, reminders, alarms, and recommended products, as well as the ability to enter data, communicate with doctors, and schedule appointments.

While in the exemplified embodiment the user interface 210 forms part of the processing device, in other embodiments the user interface can form part of a different device, including the sensor device 100 or a separate device. As used herein, the term "user interface" can refer to any component or apparatus by which a person interacts with a corresponding device. For example, a user interface can be a screen, a touch screen, a mouse, a keyboard, a button, a switch, an LED display, or any combination thereof. A user interface can provide output, input, or both.

The exemplified sensor device 100 includes its own user interface 110. In the exemplified embodiment, this user interface 110 includes controls for turning the sensor device 100 ON and OFF, thus enabling or disabling its ability to capture images of the surface 14 of the user's skin. In other embodiments, the user interface 110 can include other standard features, such as lights indicating whether the device 100 is on, controls determining the time that images will be captured, controls for controlling a light source, or a display for showing information such as the information shown by user interface 210.

The sensor device user interface 110 can also include controls for a treatment module 21 for treating a skin condition. In the exemplified embodiment, the treatment module is a light treatment module, and forms part of the sensor device 100. Thus, in this embodiment, the sensor device 100 can also function as a skin treatment device. For example, the light treatment module can include a light source for treating acne. In other embodiments, the treatment module 21 can form part of a device separate from the sensor device, and/or can use a method other than light, or can be omitted.

In one embodiment, a sensitizing agent, such as aminolevulinic acid (ALA) or methylaminolevulinate (MAL), is applied to the skin. After a short incubation period, the active ingredient is activated by the light source (e.g., a laser or a blue light source) of the light treatment module 21, thus causing a decrease in sebaceous glands and *P. acnes* bacteria. A sensor device utilizing laser diodes (LD) 121 for light treatment is shown in FIG. 26. In other embodiments, other forms of light treatment can be utilized. In yet other embodiments, light treatment can be omitted.

Figure 18:
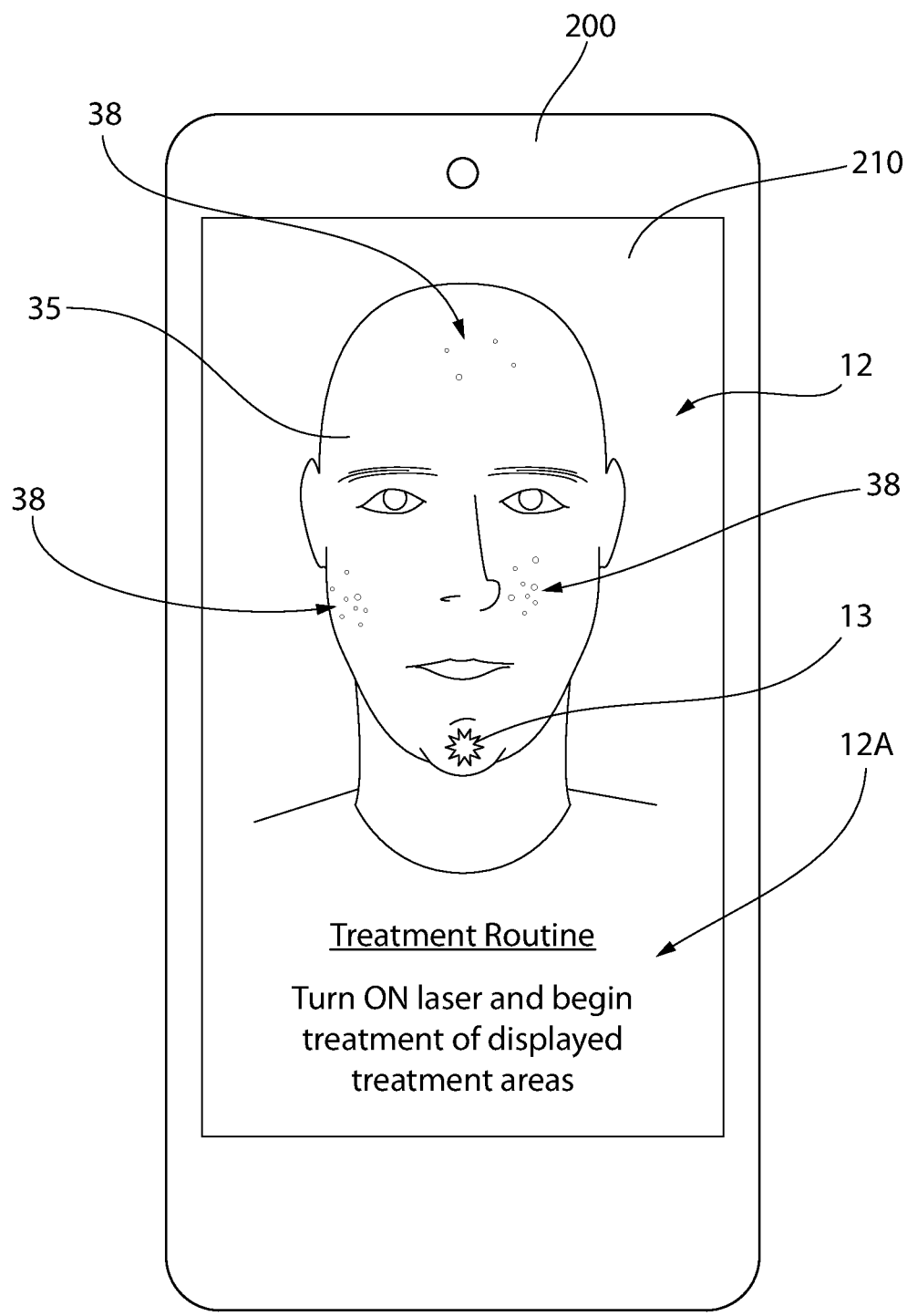
FIG. 18 shows a processing device providing a first step of a skin treatment routine according to one embodiment.

FIG. 18 shows a processing device 200 providing a first step of a skin treatment routine 12 according to one embodiment. A skin treatment routine can be understood as any type of instruction or instructions for providing skin treatment. The user interface 210 includes an image of the user's skin 35, which in this embodiment is the user's face. The image of the user's skin 35 includes treatment areas 38, that is, indicators of areas of the skin having a condition requiring treatment. These treatment areas can be identified using the sensor device. As discussed above, in the exemplified embodiment, the sensor device 100 can take images of the user's skin, and image data from these images can be stitched together to create a composite image of the user's face 35 that includes the identified treatment areas 38. The treatment areas 38 can be indicative of any type of condition and/or irregularity visible on the skin. In the exemplified embodiment, the treatment areas 38 are indicative of acne. Standard image processing methods can be used to improve the visibility of the treatment areas 38.

In this embodiment, the user interface includes a current position indicator 13 that tracks positions of a skin treatment device at it moves so that the user can see, for example, whether the user is treating the identified treatment areas 48. This feature can help guide the user to the areas requiring treatment. In the exemplified embodiment discussed in FIG. 17, the sensor device 100 includes a light treatment module 21. As shown in FIG. 26, the treatment module 21 can include laser diodes (LDs) 121 and an LD driver 159. The exemplified sensor device also includes a position sensor 130 (see FIG. 26) that is configured to generate position data indicative of a position of the sensor device. The operation of the position sensor 130 is discussed in more detail with respect to FIG. 26. This position data can be transmitted to the processing device 200. Based on this position data, the user interface 210 can display the current position indicator 13, which can indicate where the treatment module 21 is located with respect to the user's face and the treatment areas 38. Known methods of calibrating the position sensor 130 and position indicator 13 can be utilized. For example, at the beginning of use, the user can be asked to hold the light treatment module proximate to the user's nose, thus assisting the location tracking system in determining where the light treatment module is located with respect to the user's face. In other embodiments, the user can be instructed to start treatment at a specifically identified treatment area to assist the system in determining where the light treatment module is located with respect to the user's face. In yet other embodiments, an image capturing device (such as a smartphone) can be used to generate images of the while the user is carrying out the treatment session. The corresponding image data can then be processed using image recognition methods to help determine where the treatment device is positioned. In other embodiments, a treatment module location tracking system can be omitted.

In the exemplified embodiment, the skin treatment routine 12 comprises real-time instructions 12A for a user to follow during a skin treatment session. In FIG. 18, the real-time instructions 12A instruct the user to turn ON the laser of the light treatment module 21 (FIG. 17) and begin light treatment of the treatment areas 38 displayed on the image of the user's skin 35. The routine 12 can continue to show step-by-step instructions as the user proceeds in treating the treatment areas 38. In certain embodiments, the routine can include instructions to apply a photosensitizer-based topical cream or other topical solution that will enhance the performance of the treatment device in treating the skin condition.

Figure 19:
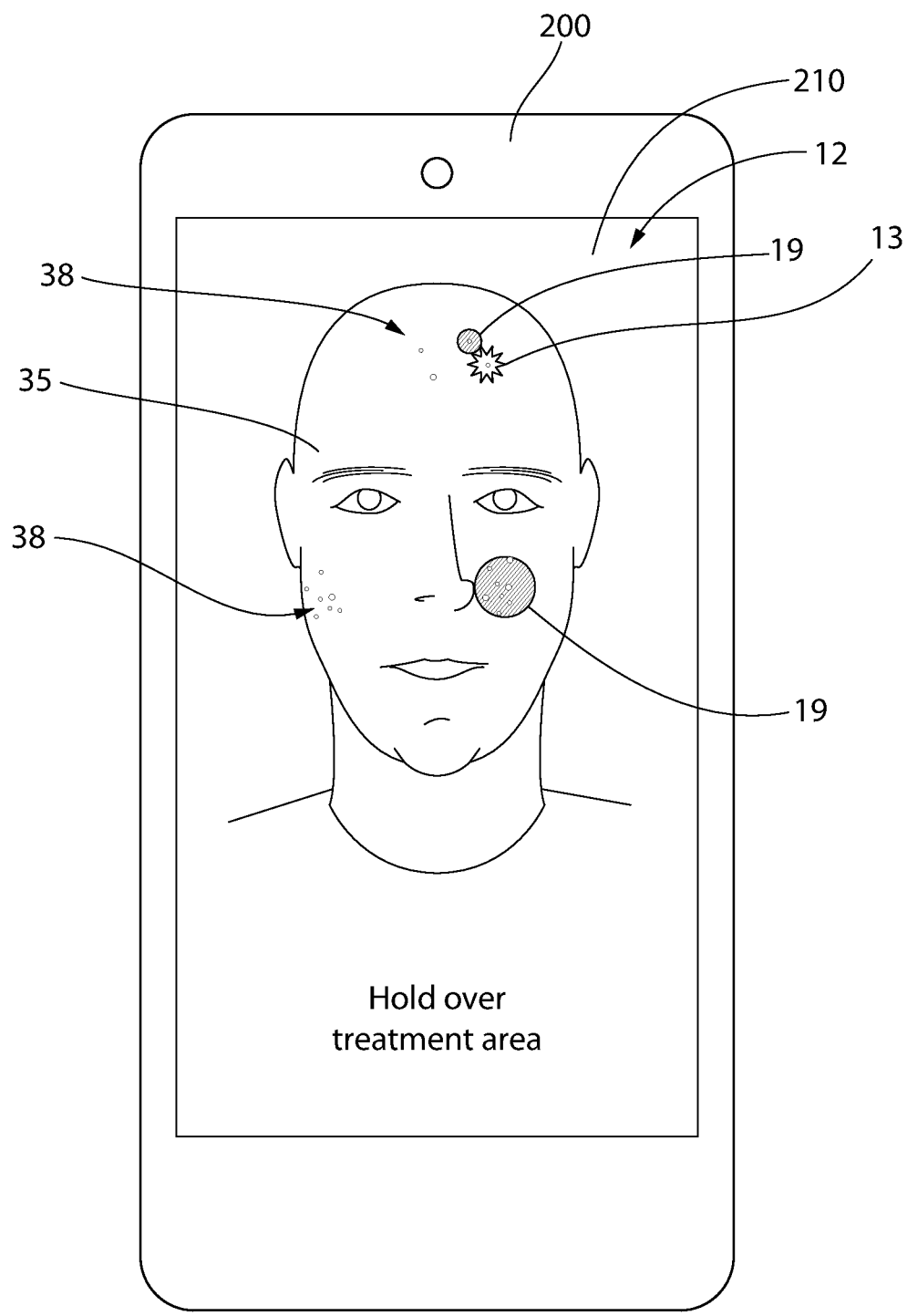
FIG. 19 shows a processing device providing a subsequent step of a skin treatment routine according to one embodiment.

FIG. 19 shows the processing device 200 providing a subsequent step of a skin treatment routine 12 according to one embodiment. The user interface 210 again provides an image of the user's skin 35 that includes identified treatment areas 38, as well as a current position indicator 13. In this embodiment, the user has begun treating his face. The treatment areas 38 not yet treated can be uniquely identified by any visual indication, for example, by being a certain shape, shading, or color (e.g., red). By contrast, treatment areas that have received adequate treatment can have a treated area indicator 19. This indicator 19 can be a visual indication, for example, a green shading over the treatment area to indicate that an area has been adequately treated. In the exemplified embodiment, the system can monitor the current position of the treatment module and, as an area receives sufficient light treatment (which can be based, for example, on the duration, wavelength, and/or power of the treatment light), can identify the area as treated using the treated area indicator 19. This can help a user to ensure that all treatment areas 38 are adequately treated.

In other embodiments, the current position indicator 13 and/or the position sensor can be omitted. Further, the instructions, rather than being real-time, can simply identify the steps that should be carried out. Such a routine, for example, can include a static image of the user's skin.

Figure 20:
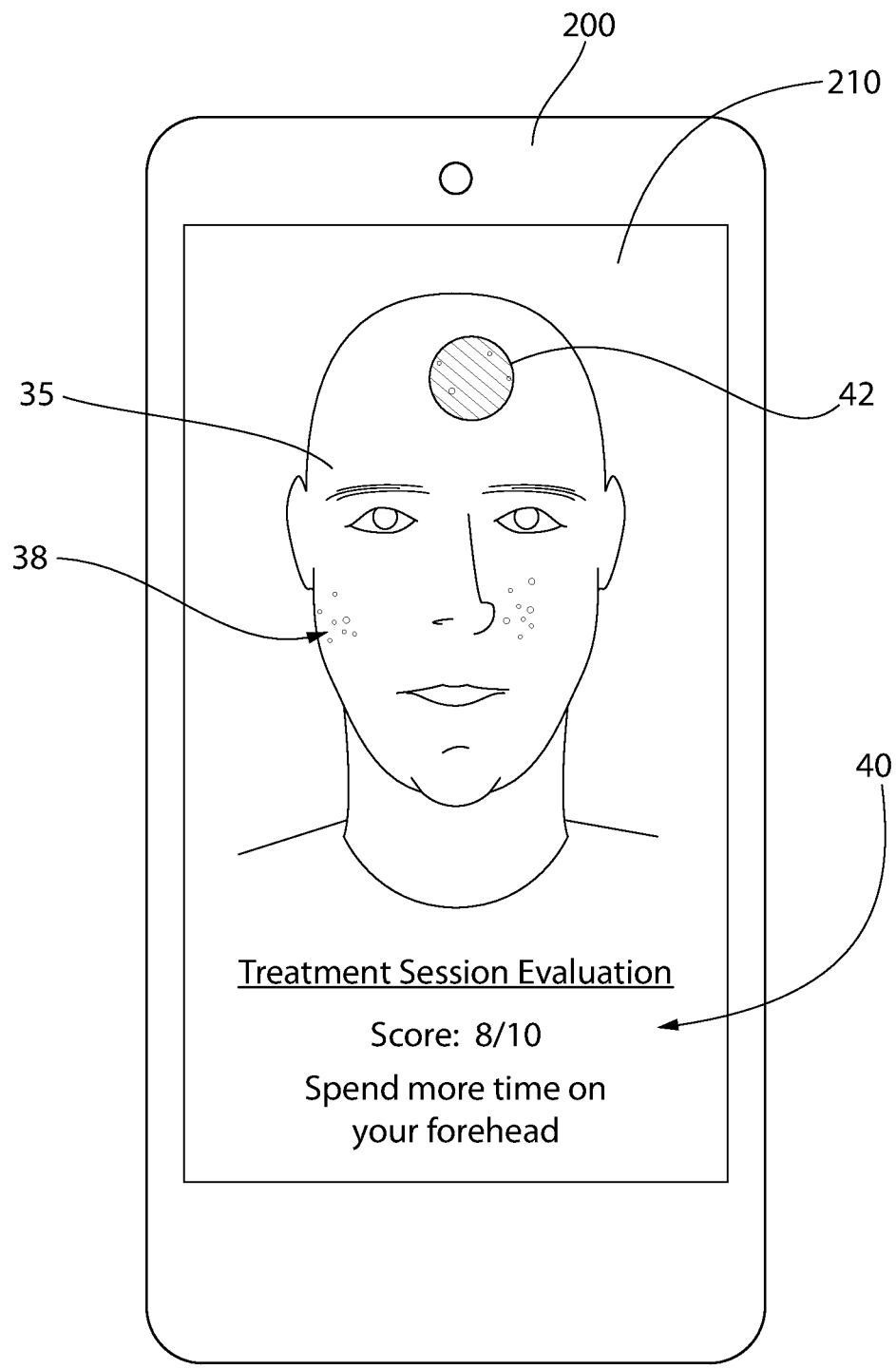
FIG. 20 shows a processing device providing a skin treatment session evaluation according to one embodiment.

FIG. 20 shows the processing device 200 providing a skin treatment session evaluation 40 according to one embodiment. As used herein, a "skin treatment session evaluation" can refer to any type of evaluation of a skin treatment session, including, but not limited to, a report or score indicating how well a user followed a skin treatment routine. In FIG. 20, the treatment session is complete and is being evaluated. The user interface 210 again provides an image of the user's skin 35 that includes identified treatment areas 38. The evaluation 40 includes an insufficient treatment indicator 42 indicating where the treatment device has not been in a position for a sufficient period of time. In FIG. 20, the insufficient treatment indicator 42 indicates that the treatment area on the user's forehead was not adequately treated. This indicator 42 can include a circle or shading or any other visual tool to identify a specific area. In the exemplified embodiment, the insufficient treatment indicator 42 comprises a red shading.

In the exemplified embodiment, the treatment session evaluation includes advice ("Spend more time on your forehead") and a score. The score can be an indication of how well the user treated his skin. The score can be based on the percentage of treatment areas that were adequately treated, or another measure, such as a more specific calculation based on the extent to which each unique treatment area was adequately treated.

In view of the foregoing, the system 10 of FIG. 17 can provide a skin care system for evaluating a skin treatment session. The system can include a treatment device 100 configured to treat a skin condition, the treatment device comprising a position sensor 130 (see FIG. 26) configured to generate position data indicative of a position of the treatment device. The system can further include a processing device 200 configured to receive the position data for the treatment device 100, and determine a skin treatment session 40 evaluation for a skin treatment session based on the position data for the treatment device 100.

Figure 21:
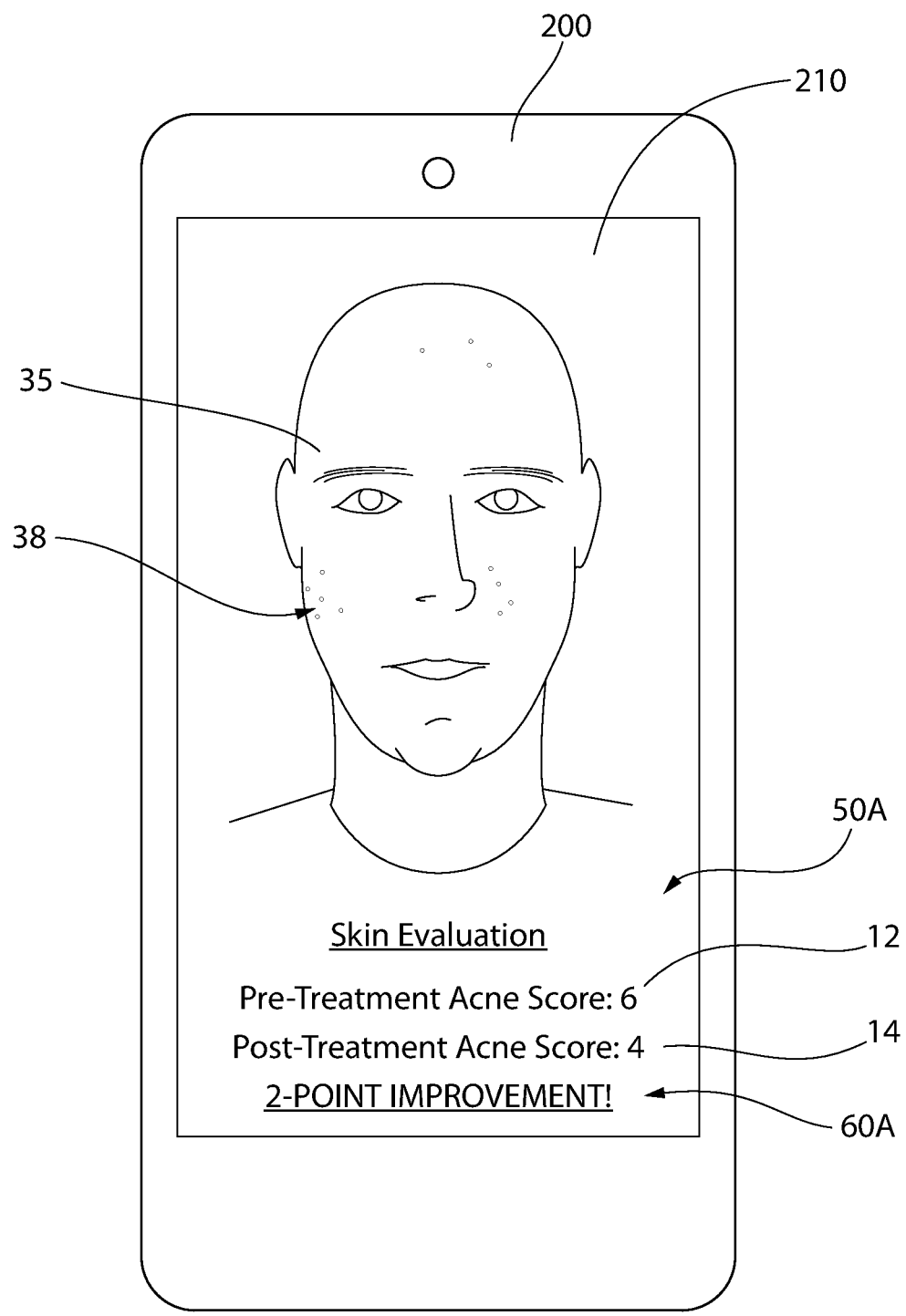
FIG. 21 shows a processing device providing a first skin evaluation according to one embodiment.

FIG. 21 shows a processing device 200 providing a first skin evaluation 50A according to one embodiment. In this embodiment, the user interface 210 again provides an image of the user's skin 35 that includes identified treatment areas 38. The user interface 210 further provides the first skin evaluation 50A. In this embodiment, the first skin evaluation 50A includes a pre-treatment acne score 12 and a post-treatment acne score 14. The first skin evaluation 50A further includes a change indicator 60A. In this figure, the acne score (scored on a scale of 0 to 10) decreased from 6 to 4 for a 2-point improvement.

In the exemplified embodiment, the acne scores 12, 14 are based on an amount of acne detected from the composite image of the user's face 35 before treatment, and an amount of acne detected from a previous composite image of the user's face 35 after treatment, respectively. In other embodiments, other time periods can be used for comparison. Certain evaluations discussed herein monitor a score change over the course of days. In other embodiments, for example, the system could monitor a weekly score over the course of months.

For determining an acne score, the processing device can utilize, for example, an algorithm using quantitative analysis to develop an index. In the exemplified embodiment, the algorithm calculates the sum of intensity of spot brightness (for the relevant emission wavelength) multiplied by the spot size across the entire set of images measured. More severe acne, or other types of skin conditions, could use different bandwidths to determine a score. The score can be any type of numerical, alphanumerical, or other visual representation of performance. In the exemplified embodiment, the score is on a scale of 0 to 10, but the embodiments are not so limited. Determining a score enables the user to receive an acne score indicative of the extent of the acne present in the imaged portion of the user's skin, and to compare this with previous scores to determine how effective a treatment has been. In other embodiments, other methods of image recognition and processing can be utilized.

Note further that, while the embodiments discussed herein refer to acne scores, a similar method can be used to determine a score for any type of skin condition, such as the different skin conditions discussed herein. For example, the system can monitor the spread or receding of a rash. A skin condition score or change in skin condition score can be used to change a treatment routine or evaluation for any type of skin condition.

Figure 22:
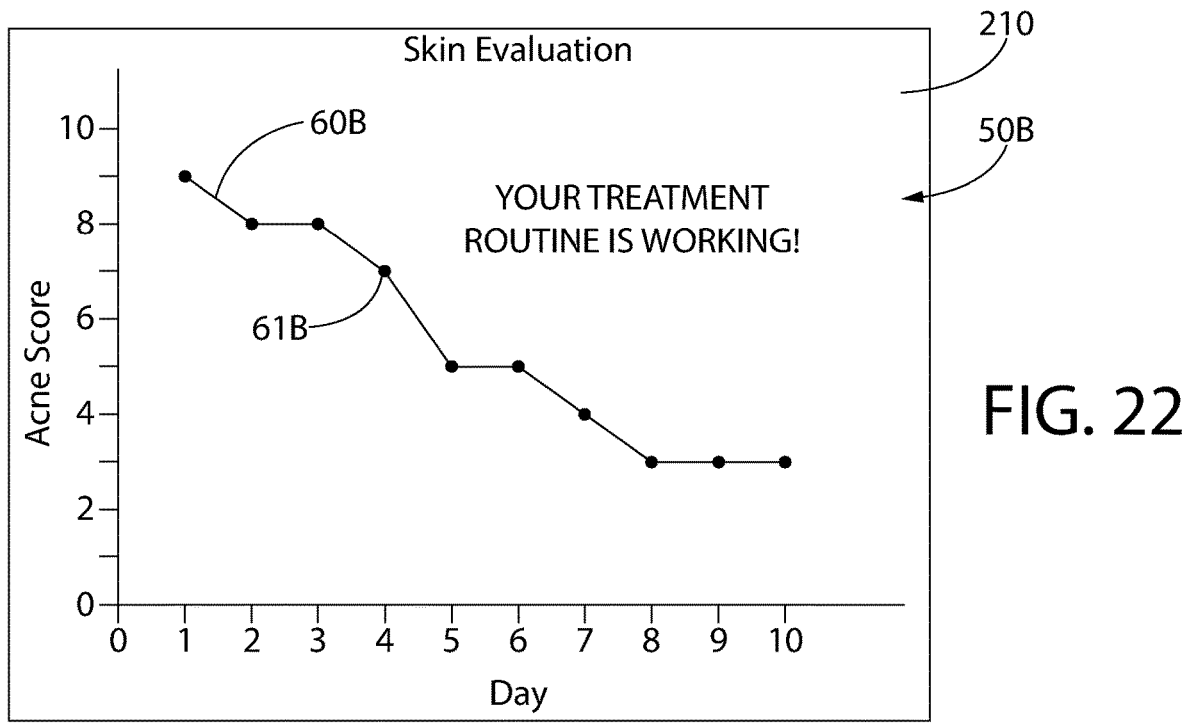
FIG. 22 shows a user interface providing a second skin evaluation according to one embodiment.

FIG. 22 shows a user interface 210 providing a second skin evaluation 50B according to one embodiment. In this figure, a graph is provided showing the change in acne score over time. The data points 61B show an acne score for each day. The change indicator 60B is a line connecting the data points 61C. By this skin evaluation 50B, a user can see a decrease in his or her acne score over time, thus indicating that the acne routine being used is working. In this embodiment, the evaluation 50B also provides feedback (YOUR TREATMENT ROUTINE IS WORKING!).

Figure 23:
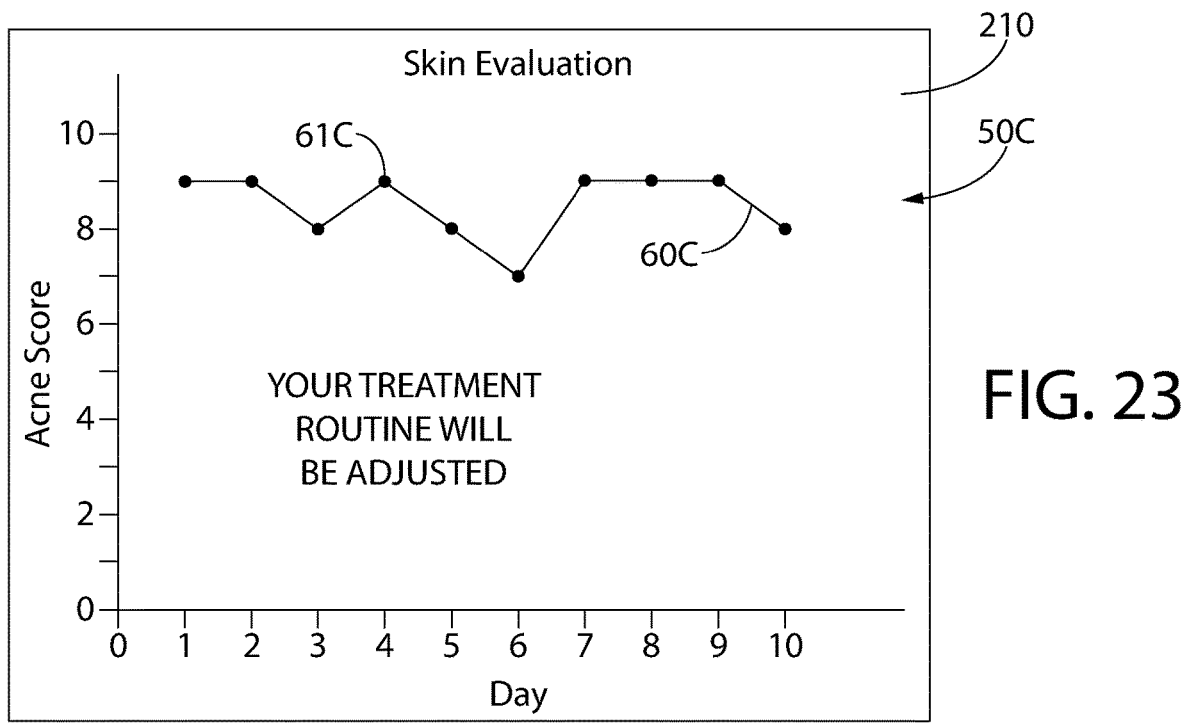
FIG. 23 shows a user interface providing a third skin evaluation according to one embodiment.

FIG. 23 shows a user interface providing a third skin evaluation 50C according to one embodiment. Similar to FIG. 22, the graph of FIG. 23 shows the change in acne score over time, with data points 61C showing an acne score for each day, and the change indicator 60C being a line connecting the data points 61C. But unlike FIG. 22, there is not a general decrease in the acne score over time. Rather, the acne score is fluctuating up and down, thus indicating that the acne routine being used is not working. The evaluation 50C provides written feedback (YOUR TREATMENT ROUTINE WILL BE ADJUSTED). Accordingly, the system can be configured to alter the treatment routine to attempt to find a more effective routine. In this manner, the system is able to monitor and adjust the treatment routine to ensure effectiveness.

Figure 24:
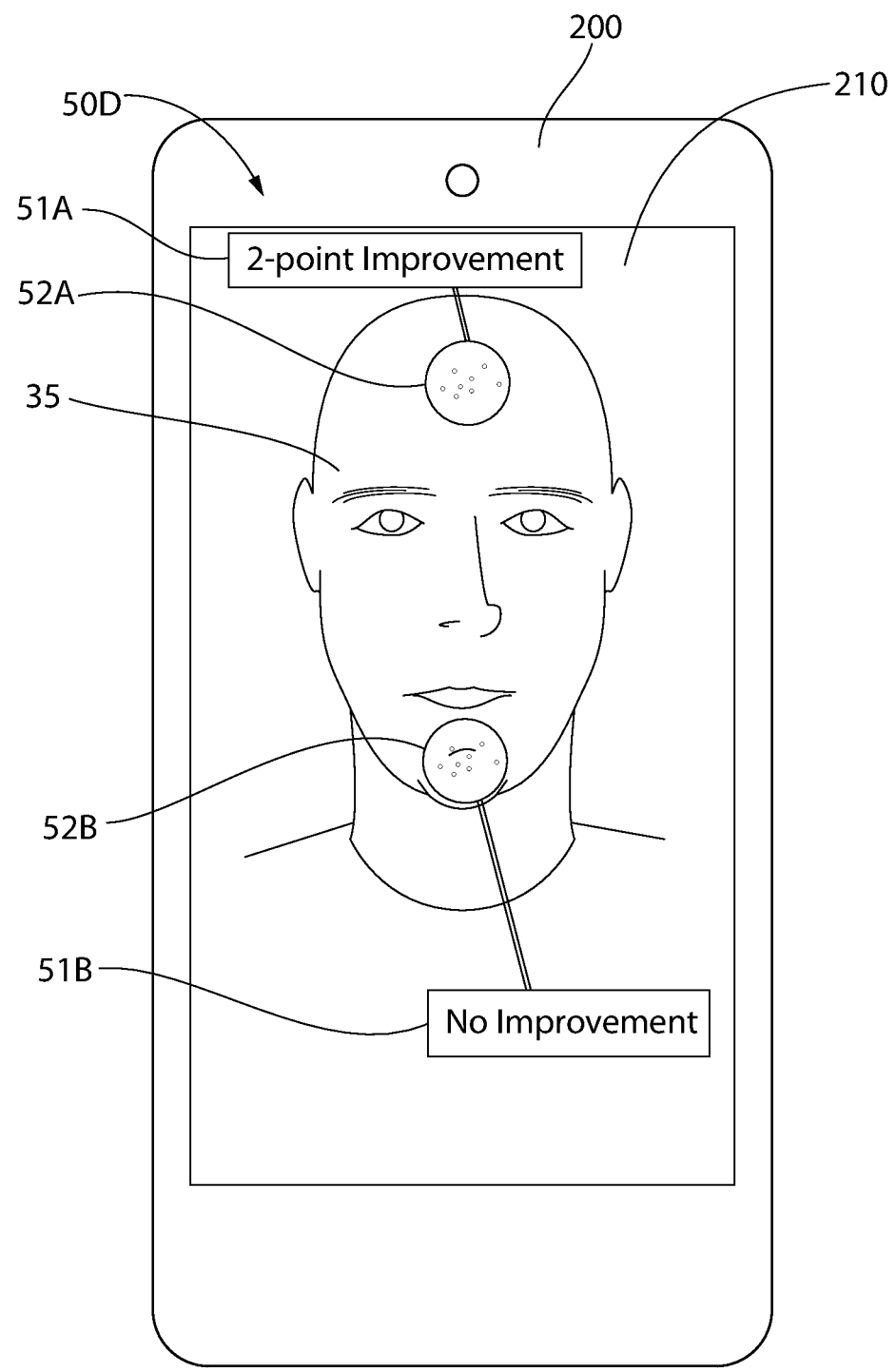
FIG. 24 shows a processing device providing a fourth skin evaluation according to one embodiment.

FIG. 24 shows a processing device 200 providing a fourth skin evaluation 50D according to one embodiment. In this embodiment, the user interface 210 displays the user's skin 35 divided into different areas, in this example, a first area 52A corresponding with the forehead, and a second area 52B corresponding with the chin. The evaluation comprises a unique skin evaluation for each area 52A, 52B. Specifically, the first area 52A has a first area evaluation 51A, and the second area 52B has a second area evaluation 51B. In the exemplified embodiment, the evaluations 51A, 51B indicate the change in score for each area. In other embodiments, the evaluation could simply state the current score.

The exemplified embodiment shows different skin evaluations for different areas of the skin. In other embodiments, the user interface 210 can provide different skin treatment routines for different areas of the skin. For example, different areas of the skin can have different laser exposure times, or receive different laser intensities or frequencies. By the above methods, greater granularity (area-by-area) can be provided in evaluation the skin, and area-specific treatment instructions can be provided.

Figure 25:
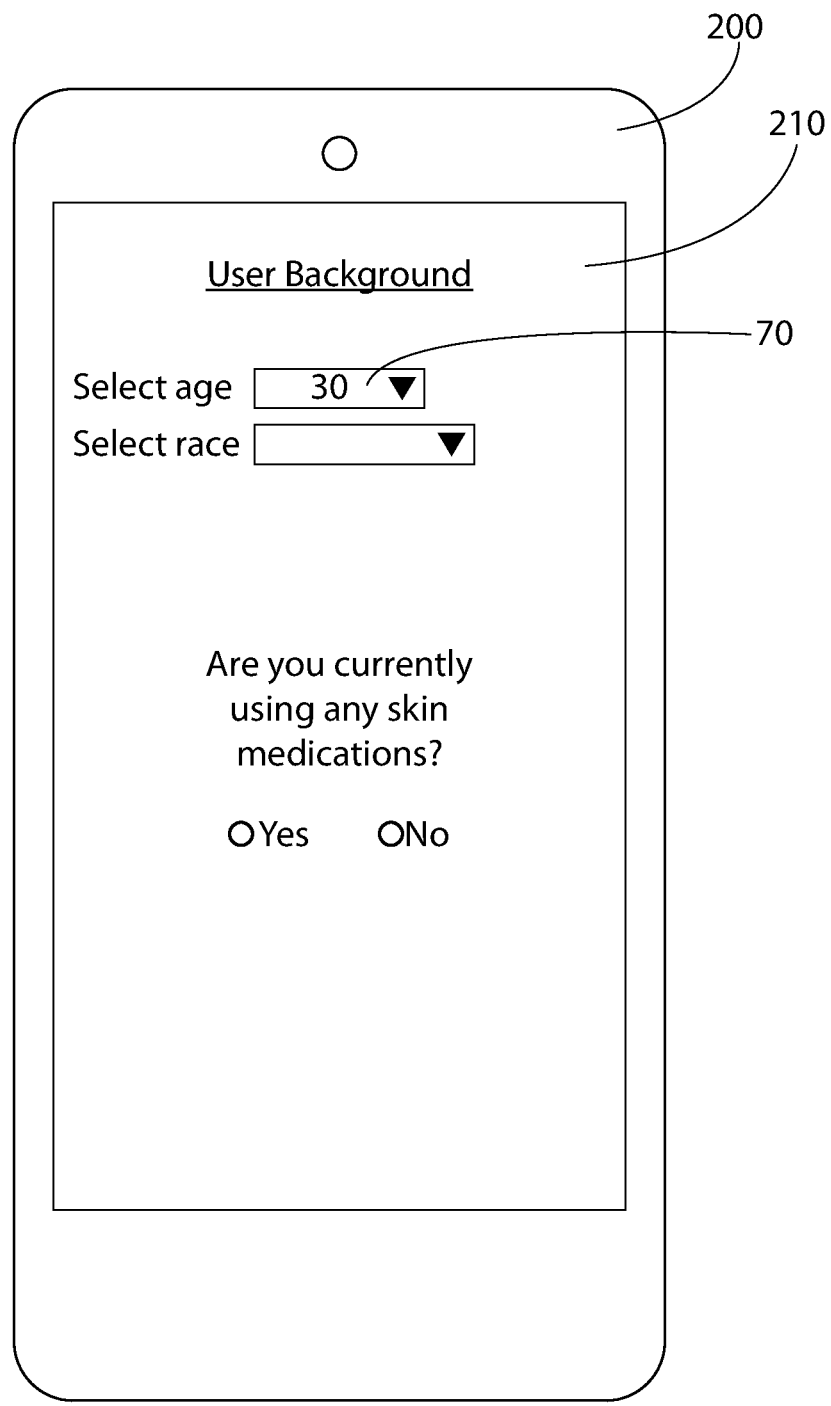
FIG. 25 shows a processing device where the user provides user skin input according to one embodiment.

FIG. 25 shows a processing device 200 where the user provides user skin input 70 according to one embodiment. In this figure, the user interface 210 enables the user to provide input 70 relevant to the user's skin. This input 70 can be used by the processing device 200 in generating its treatment routines and evaluations. For example, knowing the race of the user can help the system to determine whether a detected skin color is irregular or not. Further, certain skin types may be more easily damaged by extended exposure to light treatment, and thus the treatment routine could reflect his reality. Further, such information can be useful to a doctor evaluating data from the processing device.

FIG. 26 is a block diagram of the sensor device 100 according to one embodiment. The exemplified device 100 includes an image sensor 160, as well as readout electronics 162 for transferring the image data from the image sensor to an analog front-end system 164. For purposes of the present disclosure, the term "image data" is any type of information indicative of an image, including information extracted or derived from other information or data indicative of an image, regardless of the form of the extracted information, and combinations thereof. The image data may be in the form of mathematical data, analog data, and/or digital data.

A microcontroller 150 is operably coupled to the image sensor 160. The microcontroller 150 includes a memory 152, an analog-to-digital converter (ADC) and digital signal processor (DSP) 154, and the processor 156. The processor 156 is operably coupled to the image sensor 160 and the position sensor 130, and is configured to control the image sensor 160. For example, the processor 156 can instruct the image sensor 160 to begin collecting image data.

The exemplified microcontroller 150 and processor 156 are operably coupled to the sensor device user interface 110 discussed above. Further, the microcontroller 150 and processor 156 are operably coupled to a transmitter 166 for transmitting the image data and the position data. In the exemplified embodiment, the transmitter 166 includes an RF circuit and an antenna and is configured to transmit the image data and the position data to the processing device by wireless RF signals, though the disclosure is not so limited.

The exemplified microcontroller 150 and processor 156 are also operably coupled to a light source 120 for illuminating a surface, and a driver 158 for controlling the light source 120. In the exemplified embodiment, the light source 120 is one or more LEDs and the driver 158 is an LED driver. In other embodiments, the light source can provide any type of illumination, or can be omitted.

In the exemplified embodiment, the light source 120 is configured to generate one or more excitation wavelengths effective to cause at least one of the plurality of images to include an acne indicator indicating the presence of porphyrin, the metabolic byproduct of *Propionibacterium acnes*, in the user's face. The excitation wavelengths can be configured to cause the porphyrin in the user's face to emit orange or red fluorescence in follicle openings.

In the exemplified embodiment, the excitation wavelengths are 405 nm (blue). But as discussed above, in other embodiments, the excitation wavelengths can be other values, such as those between 390 and 420 nanometers. In other embodiments, a photosensitizer may be used on the skin such that a different wavelength (e.g., 630 nm) is effective.

In yet other embodiments, the light source can be omitted and an image sensor can capture images without the aid of a light source.

In one embodiment, the image sensor 160 can be configured to generate image data for each of a plurality of images of different portions of a user's face. In the exemplified embodiment, the images are small in the amount of surface area they capture due to the small size and pen-like shape of the handheld sensor device. Thus, the individual images are smaller than the overall area of skin that is of concern. Thus, in the exemplified embodiment, the image data from each individual image is combined to create a composite image of the user's skin or a portion thereof.

In the exemplified embodiment, the image sensor 160 is configured to capture orange or red fluorescence in at least one of the plurality of images, this fluorescence being an acne indicator. Further, the emission may be band-passed filtered to eliminate unwanted excitation light. In the exemplified embodiment, the image sensor is a charge-coupled device (CCD) image sensor using CMOS technology.

The exemplified sensor device 100 can include a lens barrel, lens, and aperture to assist the image sensor 160 in capturing images. Further, a dichroic (long pass) filter can be used for selectively passing light of a small range of colors while reflecting others.

The exemplified device 100 further includes a position sensor 130 configured to, for each image of the plurality of images, generate corresponding position data indicative of a position of the sensor device 100 when the image data was generated. As used herein, the term "position data" can refer to any type of information indicative of a position of the sensor device or a position of a component of the sensor device, including information extracted or derived from other information or data indicative of a position, regardless of the form of the extracted information, and combinations thereof. The position data may be in the form of mathematical data, analog data, and/or digital data. For example, the position data can be indicative of a spatial orientation of the sensor device and/or a motion of the sensor device. The position data can also be related to other factors, such as acceleration, velocity, or proximity to a reference point (such as a marker of a feature of the user's skin).

The processing device 200 can be configured to receive the image data and the position data for each of the plurality of images. Further, the processing device 200 can be configured to combine portions of the image data for each of the plurality of images to generate composite image data, and the composite image data can be used to generate a composite image of the user's skin. For example, the composite image data can convert small images of the user's face into a composite image of a portion (or an entirety) of the user's face. The combination of the image data can be based on the corresponding position data for each image of the plurality of images, thereby enabling the separate images from the sensor device to be aligned and stitched together. The composite image can include the treatment areas (see FIG. 18), thus providing the user a view of where acne is developing on his or her face.

The composite image data can be generated by several different means. For example, the composite image data can be generated by extracting the relative displacement of each of the plurality of images during movement of the sensor device along the user's face. Further, the composite image data can be generated using an optical translation measurement (OTM) assembly. Further, as discussed above, the composite image data can be processed such that the composite image comprises colors that allow the acne indicator to be more easily viewed.

The position sensor can be any sensor configured to generate position data. For purposes of the present disclosure, the term "position data" is any type of information indicative of a position, including information extracted or derived from other information or data indicative of a position, regardless of the form of the extracted information, and combinations thereof. The position data may be in the form of mathematical data, analog data, and/or digital data. The term "position" can refer to any information related to location, orientation, or proximity, or derivatives thereof.

In the exemplified embodiment of FIG. 26, the position sensor 130 comprises an accelerometer 132 and a three-axis gyroscope 134 for tracking the position of each of the plurality of images. This information can be used to determine how to combine the images into a composite image. In the exemplified embodiment, the images will have overlapping portions, though the disclosure is not so limited. Any type of image stitching method or other method for combining images into a composite image can be utilized.

The position sensor can also be used to track the current location of a treatment module 121 of the sensor device. FIG. 26 shows the microcontroller 150 operably coupled to a treatment driver 159 and a treatment module 121. In the exemplified embodiment, the treatment module 121 comprises laser diodes (LDs) for providing laser treatment for acne, and the treatment driver 159 comprises an LD driver. The treatment module 121 can provide light treatment of varying intensity, wavelength, and duration. In other embodiments, the treatment module can provide other types of treatments, such as application of air, water, or a topical solution for acne or other types of skin conditions.

Figure 27:
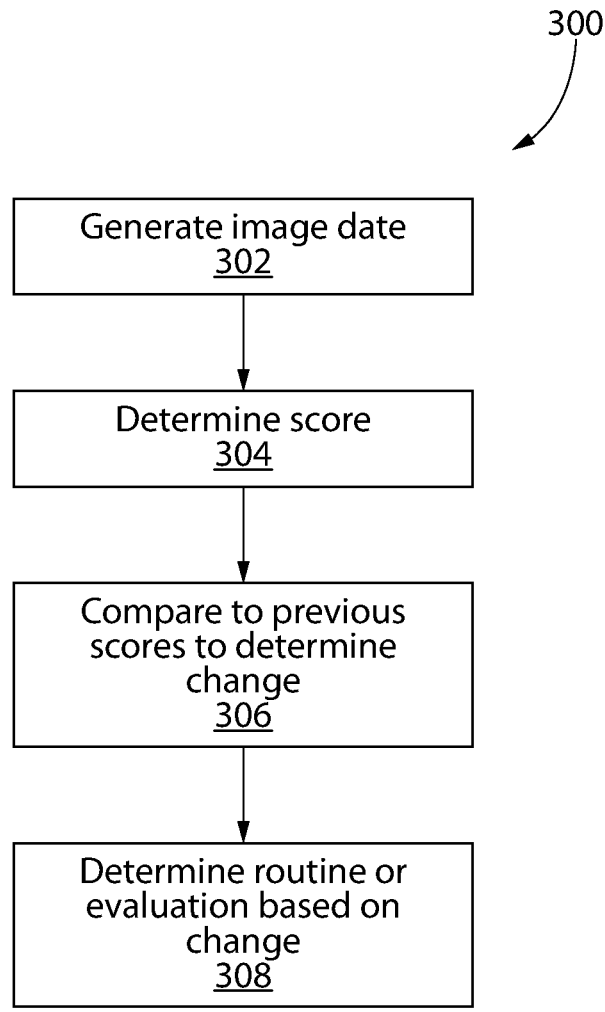
FIG. 27 shows a flow chart for determining a routine or evaluation based on a change in image data according to one embodiment.

FIG. 27 shows a flow chart 300 for determining a routine or evaluation based on a change in image data according to one embodiment. A sensor device can be configured to generate image data for each of a plurality of images of a user's skin, the plurality of images taken at different times (operation 302). As discussed above, the different times can be separated by any time interval. For example, the images can be taken before and after a treatment session, or each day after a treatment session. A processing device can be configured to receive the image data, determine a change in the image data for the different times, and determine a skin treatment routine or a skin evaluation based on the change in the image data. In the exemplified embodiment, a score is determined (operation 304). Then a comparison is made between this score and a previous score to determine a change in the score (operation 306). A routine or evaluation is determined based on the determined change in score (operation 308).

In certain embodiments, the processing device can be configured to both determine the skin treatment routine and determine the skin evaluation based on the change in the image data. Further, the skin treatment routine can be based on the skin evaluation. For example, if the skin evaluation determines that there has been an improvement to the skin over time, the routine can provide a similar routine to the previous routine. By contrast, if the skin evaluation determines that there has not been an improvement to the skin over time, the routine can provide a different routine to the previous routine.

In certain embodiments, the skin treatment routine can comprise a laser exposure time that is based on the skin evaluation. Thus, for example, if the evaluation determines a serious issue in the middle of the chin, the routine can instruct the user to provide extended laser exposure time to the middle of the chin.

Similarly, the processing device can also be configured to determine a pattern based on the received image data, and determine a skin treatment routine or a skin evaluation based on the determined pattern. Thus, for example, if the processing device determined a pattern where the skin condition would improve for 3 days, then worsen for three days, the routine could adjust based on the apparent non-effectiveness of the current routine.

Further, the determination of the skin treatment routine or the skin evaluation can be based on normalized image data. This normalization can be used, for example, to account for differing types of skin types and colors, and thus provide more reliable analysis. In one embodiment, a skin care system can include a sensor device configured to generate image data for each of a plurality of images of a user's skin, the plurality of images taken at different times, and a processing device configured to normalize the image data, and determine a skin treatment routine or a skin evaluation based on the normalized image data.

Figure 28:
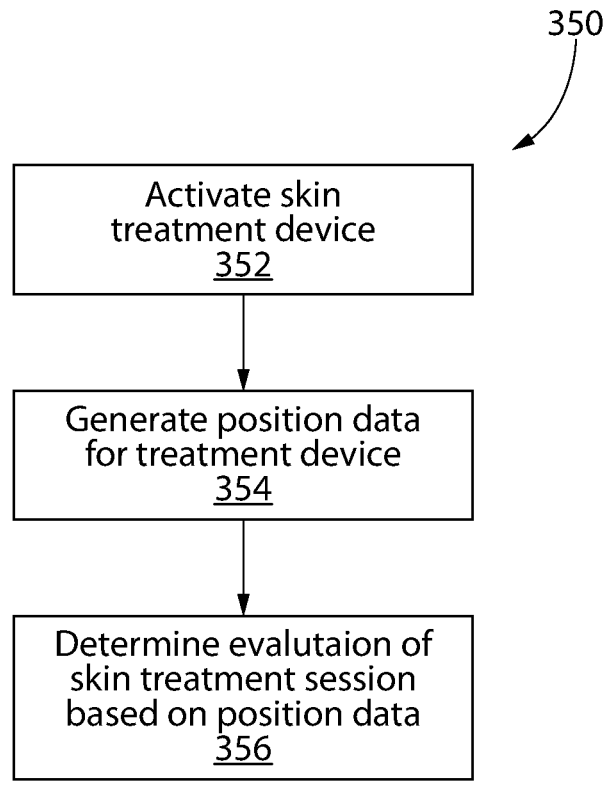
FIG. 28 shows a flow chart for determining an evaluation of a skin treatment session based on a treatment device's position data according to one embodiment.

FIG. 28 shows a flow chart 350 for determining an evaluation of a skin treatment session based on a treatment device's position data according to one embodiment. First, a skin treatment session is initiated by activating a skin treatment device (operation 352). Then position data is generated for a treatment device (operation 354). Next, an evaluation of a skin treatment session is determined based on the position data (operation 356).

In one embodiment, a skin care system includes a treatment device configured to treat a skin condition, the treatment device comprising a position sensor configured to generate position data indicative of a position of the treatment device. The system further includes a processing device configured to receive the position data for the treatment device; and determine a skin treatment session evaluation for a skin treatment session based on the position data for the treatment device. The treatment devices and skin condition feedback algorithm discussed herein can be any device and/or algorithm for treating any type of skin condition, including acne, moles, freckles, eczema, skin cancer, lupus, sores, warts, psoriasis, rosacea, hives, dry skin, crow's feet, wrinkles, and discoloring.

The skin treatment session evaluation for the skin treatment session can be based on a comparison of the position data and a provided skin treatment routine. In this manner, the system can evaluate the skin treatment session to determine, based on the location data, how well the user followed the skin treatment routine provided.

The embodiments discussed herein disclose, among other things, a method for monitoring a skin condition and determining a skin treatment routine or a skin evaluation based on changes to the monitored skin condition over a period of time. The embodiments also disclose a system for monitoring how effectively a user is carrying out a skin treatment. These methods can be performed without the inconvenience of visiting a dermatologist's office, while the information gathered can be made available to dermatologists and other health professionals. The embodiments can track the changes to a skin condition over time, and base the routine or evaluation on those changes.

Example Claim 1: A skin care system comprising: a sensor device configured to generate image data for each of a plurality of images of a user's skin taken at different times; and a processing device configured to: receive the image data; determine a change in the image data for the different times; and determine a skin treatment routine or a skin evaluation based on the change in the image data.

Example Claim 2: The system of any of the preceding claims wherein the processing device is configured to both determine the skin treatment routine and determine the skin evaluation based on the change in the image data.

Example Claim 3: The system of claim 2 wherein the skin treatment routine is based on the skin evaluation.

Example Claim 4: The system of any of the preceding claims wherein the skin treatment routine comprises a laser exposure time that is based on the skin evaluation.

Example Claim 5: The system of any of the preceding claims wherein the processing device is further configured to: determine a pattern based on the received image data; and determine a skin treatment routine or a skin evaluation based on the determined pattern.

Example Claim 6: The system of any of the preceding claims further comprising a user interface configured to display the skin treatment routine or the skin evaluation.

Example Claim 7: The system of claim 6 wherein the user interface forms part of the processing device.

Example Claim 8: The system of any of the preceding claims wherein the processing device comprises a user interface configured to receive a user skin input from a user.

Example Claim 9: The system of any of the preceding claims wherein the processing device comprises a user interface configured to display the skin treatment routine.

Example Claim 10: The system of claim 9 wherein the displayed skin treatment routine comprises an image of the skin that indicates areas of the skin requiring treatment.

Example Claim 11: The system of claim 10 wherein the skin treatment routine comprises real-time instructions for a user to follow during a skin treatment session.

Example Claim 12: The system of claim 11 wherein the user interface is configured to display a current position indicator that tracks positions of a skin treatment device.

Example Claim 13: The system of claim 12 wherein the processing device is further configured to determine a skin treatment session evaluation based on the determined skin treatment routine and the positions of the skin treatment device.

Example Claim 14: The system of any of the preceding claims wherein the user's skin has different areas, and the change in the image data comprises a change corresponding with each of the different areas of the user's skin.

Example Claim 15: The system of claim 14 wherein the skin treatment routine or the skin evaluation comprises a unique skin treatment routine or skin evaluation for each of the different areas of the user's skin.

Example Claim 16: The system of any of the preceding claims wherein the sensor device is a handheld device.

Example Claim 17: The system of any of the preceding claims wherein the determination of the skin treatment routine or skin evaluation comprises determining a skin treatment routine for treating acne or determining an acne evaluation.

Example Claim 18: The system of any of the preceding claims wherein the sensor device is enclosed by a housing separate from a housing of the processing device.

Example Claim 19: The system of any of the preceding claims further comprising a skin treatment device, the skin treatment device forming part of the sensor device.

Example Claim 20: The system of any of the preceding claims wherein the sensor device further comprises a transmitter configured to transmit the image data to the processing device by at least one wireless RF signal.

Example Claim 21: The system of any of the preceding claims wherein the processing device is a smartphone in wireless communication with the sensor device.

Example Claim 22: The system of any of the preceding claims wherein the processing device and the sensor device form part of a smartphone.

Example Claim 23: The system of any of the preceding claims wherein the determination of the skin treatment routine or the skin evaluation is based on normalized image data.

Example Claim 24: The system of any of the preceding claims wherein a user interface displays the skin evaluation, the displayed skin evaluation including a change indicator based on the change in the image data.

Example Claim 25: The system of claim 24 wherein the change indicator comprises at least one of a number, a letter, a color, a graph, shading, hatching, and images.

Example Claim 26: The system of claim 25 wherein the change indicator comprises: a first acne score indicative of an amount of acne detected at a first time; and a second acne score indicative of an amount of acne detected at different, second time.

Example Claim 27: The system of any of the preceding claims wherein: the image data for each of the plurality of images is generated from a plurality of close-range images, the close-range image data being combined based on position data corresponding with each of the close-range images; and the position data is received from a position sensor configured to, for each of the close-range images of the plurality of close-range images, generate the corresponding position data indicative of a position of a sensor device when the close-range image data was generated.

Example Claim 28: The system of claim 27 wherein: the position data is indicative of (a) a spatial orientation of sensor device, or (b) a motion of the sensor device; and the sensor device comprises an accelerometer or a three-axis gyroscope for tracking the position corresponding with each of the close-range images.

Example Claim 29: A skin care method comprising: generating, by a sensor device, image data for each of a plurality of images of a user's skin taken at different times; receiving the image data at a processing device; determining a change in the image data for the different times; and determining a skin treatment routine or a skin evaluation based on the change in the image data.

Example Claim 30: The method of claim 29 wherein the processing device is configured to both determine the skin treatment routine and determine the skin evaluation based on the change in the image data.

Example Claim 31: The method of claim 30 wherein the skin treatment routine is based on the skin evaluation.

Example Claim 32: The method of any of claims 29-31 wherein the skin treatment routine comprises a laser exposure time that is based on the skin evaluation.

Example Claim 33: The method of any of claims 29-32 further comprising: determining a pattern based on the received image data; and determining a skin treatment routine or a skin evaluation based on the determined pattern.

Example Claim 34: The method of any of claims 29-33 wherein a user interface is configured to display the skin treatment routine or the skin evaluation.

Example Claim 35: The method of claim 34 wherein the user interface forms part of the processing device.

Example Claim 36: The method of any of claims 29-35 wherein the processing device comprises a user interface configured to receive a user skin input from a user.

Example Claim 37: The method of any of claims 29-36 wherein the processing device comprises a user interface configured to display the skin treatment routine.

Example Claim 38: The method of claim 37 wherein the displayed skin treatment routine comprises an image of the skin that indicates areas of the skin requiring treatment.

Example Claim 39: The method of claim 38 wherein the skin treatment routine comprises real-time instructions for a user to follow during a skin treatment session.

Example Claim 40: The method of claim 39 further comprising displaying, by the user interface, a current position indicator that tracks positions of a skin treatment device.

Example Claim 41: The method of claim 40 wherein the processing device is further configured to determine a skin treatment session evaluation based on the determined skin treatment routine and the positions of the skin treatment device.

Example Claim 42: The method of any of claims 29-41 wherein the user's skin has different areas, and the change in the image data comprises a change corresponding with each of the different areas of the user's skin.

Example Claim 43: The method of claim 42 wherein the skin treatment routine or the skin evaluation comprises a unique skin treatment routine or skin evaluation for each of the different areas of the user's skin.

Example Claim 44: The method of any of claims 29-43 wherein the sensor device is a handheld device.

Example Claim 45: The method of any of claims 29-44 wherein the determination of the skin treatment routine or skin evaluation comprises determining a skin treatment routine for treating acne or determining an acne evaluation.

Example Claim 46: The method of any of claims 29-45 wherein the determination of the skin treatment routine or the skin evaluation is based on normalized image data.

Example Claim 47: The method of any of claims 29-46 wherein a user interface displays the skin evaluation, the displayed skin evaluation including a change indicator based on the change in the image data.

Example Claim 48: The method of claim 47 wherein the change indicator comprises at least one of a number, a letter, a color, a graph, shading, hatching, and images.

Example Claim 49: The method of claim 48 wherein the change indicator comprises: a first acne score indicative of an amount of acne detected at a first time; and a second acne score indicative of an amount of acne detected at different, second time.

Example Claim 50: The method of any of claims 29-49 wherein: the image data for each of the plurality of images is generated from a plurality of close-range images, the close-range image data being combined based on position data corresponding with each of the close-range images; and the position data is received from a position sensor configured to, for each of the close-range images of the plurality of close-range images, generate the corresponding position data indicative of a position of a sensor device when the close-range image data was generated.

Example Claim 51: The method of claim 50 wherein: the position data is indicative of (a) a spatial orientation of sensor device, or (b) a motion of the sensor device; and the sensor device comprises an accelerometer or a three-axis gyroscope for tracking the position corresponding with each of the close-range images.

Example Claim 52: A skin care system comprising: a treatment device configured to treat a skin condition, the treatment device comprising a position sensor configured to generate position data indicative of a position of the treatment device; and a processing device configured to: receive the position data from the treatment device; and determine a skin treatment session evaluation for a skin treatment session based on the position data for the treatment device.

Example Claim 53: The system of claim 52 further comprising a user interface operably coupled to the processing device, the user interface configured to display the skin treatment session evaluation.

Example Claim 54: The system of any of claims 52-53 wherein the user interface is further configured to display a skin treatment routine, the skin treatment session evaluation for the skin treatment session being based on a comparison of the position data and the displayed skin treatment routine.

Example Claim 55: The system of any of claims 52-54 wherein the user interface is further configured to display a skin treatment routine, the displayed skin treatment routine comprising an image of a user's skin that indicates portions of the user's skin requiring skin treatment from the treatment device.

Example Claim 56: The system of any of claims 52-55 wherein the user interface is further configured to display a skin treatment routine, the skin treatment routine comprising real-time instructions for a user to follow during a skin treatment session.

Example Claim 57: The system of any of claims 52-56 wherein, based on the position data, the user interface displays a current position indicator that tracks positions of the skin treatment device.

Example Claim 58: The system of any of claims 52-57 wherein the user interface displays an indicator indicating whether the treatment device has been in a position for a sufficient period of time.

Example Claim 59: The system of any of claims 52-58 wherein the user interface displays an indicator indicating all positions where the treatment device was in a position for a sufficient period of time.

Example Claim 60: The system of any of claims 52-59 wherein the user interface displays an insufficient treatment indicator indicating where the treatment device has not been in a position for a sufficient period of time.

Example Claim 61: A skin care method comprising: activating a treatment device configured to treat a skin condition, the treatment device comprising a position sensor; generating, by the position sensor, position data indicative of a position of the treatment device; receiving, at a processing device, position data from the treatment device; and determining a skin treatment session evaluation for a skin treatment session based on the position data for the treatment device.

Example Claim 62: The method of claim 61 wherein a user interface is operably coupled to the processing device, the user interface configured to display the skin treatment session evaluation.

Example Claim 63: The method of any of claims 61-62 wherein the user interface displays a skin treatment routine, the skin treatment session evaluation for the skin treatment session being based on a comparison of the position data and the displayed skin treatment routine.

Example Claim 64: The method of any of claims 61-63 wherein the user interface displays a skin treatment routine, the displayed skin treatment routine comprising an image of a user's skin that indicates portions of the user's skin requiring skin treatment from the treatment device.

Example Claim 65: The method of any of claims 61-64 wherein the user interface displays a skin treatment routine, the skin treatment routine comprising real-time instructions for a user to follow during a skin treatment session.

Example Claim 66: The method of any of claims 61-65 wherein, based on the position data, the user interface displays a current position indicator that tracks positions of the skin treatment device.

Example Claim 67: The method of any of claims 61-66 wherein the user interface displays an indicator indicating whether the treatment device has been in a position for a sufficient period of time.

Example Claim 68: The method of any of claims 61-67 wherein the user interface displays an indicator indicating all positions where the treatment device was in a position for a sufficient period of time.

Example Claim 69: The method of any of claims 61-68 wherein the user interface displays an insufficient treatment indicator indicating where the treatment device has not been in a position for a sufficient period of time.

Example Claim 70: A skin care system comprising: a sensor device configured to generate image data for each of a plurality of images of a user's skin taken at different times; and a processing device configured to: normalize the image data; and determine a skin treatment routine or a skin evaluation based on the normalized image data.

Example Claim 71: A skin care method comprising: generating, by a sensor device, image data for each of a plurality of images of a user's skin taken at different times; normalizing, by a processing device, the image data; and determining a skin treatment routine or a skin evaluation based on the normalized image data.

While the inventions have been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A personal care implement comprising:
   an emitting end;
   an electromagnetic source for projecting electromagnetic radiation onto an area of skin, the electromagnetic source having emission characteristics to treat a skin condition;
   a light sensor configured to sense an amount of ambient light present at the emitting end; and
   a controller that instructs the electromagnetic source to begin projecting only when the light sensor senses that the amount of ambient light at the emitting end is below a predefined threshold;
   a timer, the controller being configured to instruct the electromagnetic source to project the electromagnetic radiation for a predetermined period of time measured by the timer each instance that the electromagnetic source is activated; and
   wherein upon each activation of the electromagnetic source, the electromagnetic source continues to project the electromagnetic radiation for the predetermined period of time even if the light sensor senses that the amount of ambient light at the emitting end is above the predetermined threshold.

2. The personal care implement of claim 1 further comprising
   a body section;
   a treatment section including the emitting end and a body end, the emitting end being located at a distal end of the treatment section and opposite the body end, the body end being attached to the body section, the treatment end being formed as a seal; and
   a pressure sensor configured to sense a pressure exerted by the treatment area on the treatment end of the treatment section,
   wherein the controller instructs the electromagnetic source to begin projecting only when (1) the light sensor senses the amount of ambient light at the emitting end of the treatment section is below the predefined threshold, and (2) the pressure sensor senses the pressure exerted by the area of the skin on the treatment end of the treatment section is above a predefined pressure.

3. The personal care implement of claim 2 wherein once the electromagnetic source is activated to project the electromagnetic radiation, the electromagnetic source continues to project the electromagnetic radiation for the predetermined period of time even if the pressure sensor senses the pressure exerted by the area of the skin on the emitting end is below the predefined pressure.

4. The personal care implement of claim 1 further comprising a movable joint that attaches the treatment section to the body section.

5. The personal care implement of claim 4 wherein the pressure sensor senses a movement of the movable joint.

6. The personal care implement of claim 4 wherein the movable joint is a telescoping joint.

7. The personal care implement of claim 4 wherein the movable joint comprises bellows.

8. The personal care implement of claim 4 wherein the movable joint is a pivoting joint.

9. The personal care implement of claim 1 wherein the emitting section is fixed relative to the body.

10. The personal care implement of claim 1 wherein the predetermined threshold of the light sensor is an amount of light present outside of the emitting end.

* * * * *